(12) United States Patent
Prockop et al.

(10) Patent No.: US 6,562,613 B2
(45) Date of Patent: May 13, 2003

(54) RECOMBINANT C-PROTEINASE AND PROCESSES, METHODS AND USES THEREOF

(75) Inventors: Darwin J. Prockop, Philadelphia, PA (US); Yoshio Hojima, Philadelphia, PA (US); Shi-Wu Li, Collingswood, NJ (US); Aleksander Sieron, Conshohocken, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/850,048

(22) Filed: May 7, 2001

(65) Prior Publication Data

US 2002/0037574 A1 Mar. 28, 2002

Related U.S. Application Data

(62) Division of application No. 08/872,757, filed on Jun. 10, 1997, now Pat. No. 6,258,584, which is a division of application No. 08/609,187, filed on Mar. 1, 1996, now abandoned.
(60) Provisional application No. 60/002,038, filed on Aug. 8, 1995.

(51) Int. Cl.[7] .......................... C12N 9/50; C12N 15/09; C12N 1/20; C12N 15/00; C07H 21/04
(52) U.S. Cl. .................. 435/219; 435/252.3; 435/320.1; 435/69.2; 536/23.2; 536/23.5; 530/350
(58) Field of Search ................................ 435/69.2, 219, 435/252.3, 252.33, 320.1; 530/350; 536/23.2, 23.5

(56) References Cited

PUBLICATIONS

Davidson et al., "Procollagen Processing: Limited Proteolysis of COOH–Terminal Extension Peptides by a Cathepsin-Like Protease Secreted by Tendon Fibroblasts," *Eur. J. Biochem.* 100:551 (1979).
Duskin et al., "The Role of Glycosylation in the Enzymatic Conversion of Procollagen Collagen: Studies using Tunicamycin and Concanavalin A," *Arch. Biochem. Biophys.* 185(2):326–332 (1978).
Fertala et al., "Self–Assembly into Fibrils of Collagen II by Enzymic Cleavage of Recombinant Procollagen II," *J. Biol. Chem.* 269(15):11584 (1994).
Goldberg et al., "Procollagen Peptidase: Its Mode of Action on the Native Substrate," *Cell* 4:45–50 (1975).
Hojima et al., "Type I Procollagen Carboxyl–Terminal Proteinase From Chick Embryo Tendons," *J. Biol. Chem.* 260(29):15996–16003 (1985).
Kessler et al., "Partial Purification and Characterization of a Procollagen C–Proteinase from the Culture Medium of Mouse Fibroblasts," *Collagen Relat. Res.* 6:249–266 (1986).
Kessler and Adar, "Type I Procollagen C–Proteinase From Mouse Fibroblasts: Purification and Demonstration of a 55–kDa Enhancer Glycoprotein," *Eur. J. Biochem.* 186:115–121 (1989).
Kessler and Goldberg, "A Method for Assaying the Activity of the Endopeptidase Which Excises the Nonhelical Carboxyterminal Extensions from Type I Procollagen", *Anal. Biochem.* 86:463–469 (1978).
Leung et al., "Separate Amino and Carboxyl Procollagen Peptidases in Chick Embryo Tendon," *J. Biol. Chem.* 254(1):224–232 (1979).
Njieha et al., "Partial Purification of a Procollagen C–Proteinase. Inhibition by Synthetic Peptides and Sequential Cleavage of Type I Procollagen," *Biochemistry* 23:757–764 (1982).
Ryhänen et al., "Conversion of Type II Procollagen to Collagen In Vitro: Removal of the Caroxy–Terminal Extension is Inhibited by Several Naturally Occurring Amino Acids, Polyamines, and Structurally Related Compounds," *Arch. Biochem. Biophys.* 215(1):230–236 (1982).
Takahara et al., "Type I Procollagen COOH–Terminal Proteinase Enhancer Protein: Identification, Primary Structure, and Chromosomal Localization of the Cognate Human Gene (PCOLCE)," *J. Biol. Chem.* 269(42):26280–26285 (1994).
Titani et al., "Amino Acid Sequence of a Unique Protease from the Crayfish *Astacus fluviatilis,*" *Biochemistry* 26:222–226 (1987).
Wozney et al., "Novel Regulators of Bone Formation: Molecular Clones and Activities," *Science* 242:1528–15347 (1988).

*Primary Examiner*—Tekchand Saidha
(74) *Attorney, Agent, or Firm*—Robins & Pasternak LLP

(57) ABSTRACT

The present invention is directed to the isolation and identification of the nucleic acid sequence encoding C-proteinase, the recognition of such protein's activity and applications, and tools, processes, and methods of use thereof.

10 Claims, 20 Drawing Sheets

C-Proteinase Activity

Enzyme

Figure 1A:
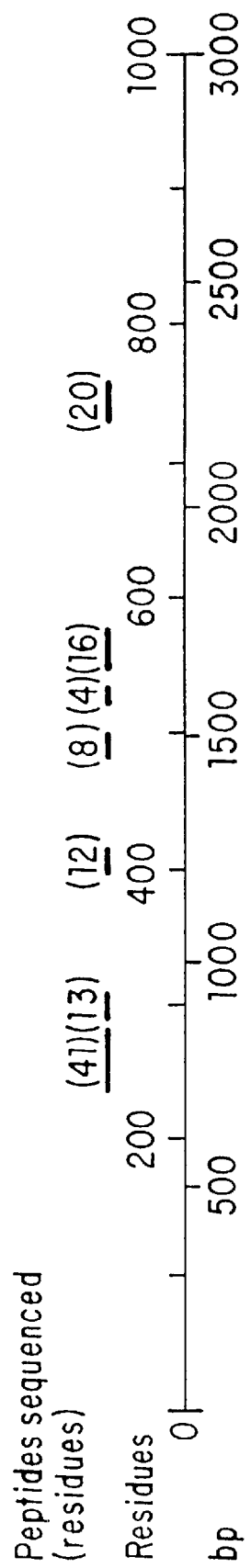

Chick Embryo    −   −   −   −   −   +
Recombinant    +   +   +   +   −   −

-pNα1
-pNα2

-C 1
-C 2

FIG. 6A

```
PCP-1 -> 1-phase Translation

DNA sequence    2458 b.p.    ATGCCCGGCGTG ... CCTGGGTCCTGC    linear

1 /   1                                                             31 /  11
ATG CCC GGC GTG GCC CGC CTG CCG CTG CTG GGG CTG CTC CTG CTC CCG CGT CCC GGC
met pro gly val ala arg leu pro leu leu gly leu leu leu leu pro arg pro gly
 61 /  21                                                             91 /  31
CGG CCG CTG GAC TTG GCC GAC TAC ACC TAT GAC CTG GCG GAG GAC GAC TCG GAG CCC
arg pro leu asp leu ala asp tyr thr tyr asp leu ala glu asp asp ser glu pro
121 /  41                                                            151 /  51
CTC AAC TAC AAA GAC CCC TGC AAG GCG GCT TTT CTT GGG GAC ATT GCC CTG GAC GAA
leu asn tyr lys asp pro cys lys ala ala phe leu gly asp ile ala leu asp glu
181 /  61                                                            211 /  71
GAG GAC CTG AGG GCC TTC CAG GTA CAG CAG GCT GTG GAT CTC AGA CGG CAC ACA GCT CGT
glu asp leu arg ala phe gln val gln gln ala val asp leu arg arg his thr ala arg
241 /  81                                                            271 /  91
AAG TCC ATC AAA GCT GCA GTT CCA GGA AAC ACT TCT ACC CCC AGC TGC CAG AGC ACC
lys ser ile lys ala ala val pro gly asn thr ser thr pro ser cys gln ser thr
301 / 101                                                            331 / 111
AAC GGG CAG CCT CAG AGG GGA GCC TGT GGG AGA TGG AGA GGT AGA TCC CGT AGC CGG CGG
asn gly gln pro gln arg gly ala cys gly arg trp arg gly arg ser arg arg arg
361 / 121                                                            391 / 131
GCG ACG TCC CGA CCA GAG CGT GTG TGG CCC GAT GGG GTC ATC CCC TTT GTC ATT GGG
ala thr ser arg pro glu arg val trp pro asp gly val ile pro phe val ile gly
421 / 141                                                            451 / 151
GCA AAC TTC ACT GGT AGC CAG AGG GCA GTC CGG TTC CGG CAG GCA ATG AGG CAC TGG GAG AAG
ala asn phe thr gly ser gln arg ala val arg phe arg gln ala met arg his trp glu lys
```

```
481 /                                                             511 /                                       171
CAC ACC TGT GTC ACC TTC CTG GAG CGC ACT GAG CGC ACT GAC AGC TAT ATT GTG TTC ACC TAT
his thr cys val thr phe leu glu arg thr asp glu arg thr asp ser tyr ile val phe thr tyr
541 /                                                                                              191
                                         181
CGA CCT TGC GGG TGC TGC GGG CCC CAG GCC ATC TCC
arg pro cys gly cys cys gly gly gly gly pro gln ala ile ser
601 /                                                             631 /                                       211
                                         201
ATC GGC AAG AAC TGT GAC AAG TTC GGC ATT GTC CAC GTC GGC CAC GTC GTC GGC
ile gly lys asn cys asp lys phe gly ile val his glu leu gly his val val gly
661 /                                                             691 /                                       231
                                         221
TTC CAC GAA CAC ACT CGG CCA GAC CGC GAC CGT TCC ATC GTT CGT GAG AAC
phe his glu his thr arg pro asp arg asp arg val ser ile val arg glu asn
721 /                                                             751 /                                       251
                                         241
ATC CAG GGG CAG GAG TAT AAC TTC CTG AAG ATG CTG AAG ATG CTG GAG GTG GAG TCC CTG
ile gln pro gly gln glu tyr asn phe leu lys met glu lys met pro gln glu val glu ser leu
781 /                                                             811 /                                       271
                                         261
GGG GAG ACC TAT GAC TTC GAC AGC ATC ATG CAT TAC GCT CGG AAC ACA TTC TCC AGG GGC
gly glu thr tyr asp phe asp ser ile met his tyr ala arg asn thr phe ser arg gly
841 /                                                             871 /                                       291
                                         281
ATC TTC CTG GAT ACC ATT GTC CCC AAG TAT GAG GTG AAC GGG GTG AAA CCT CCC ATT GGC
ile phe leu asp thr ile val pro lys tyr glu val asn gly val lys pro pro ile gly
901 /                                                             931 /                                       311
                                         301
CAA AGG ACA CGG CTC AGC AAG GGG GAC ATT GCC CAA GCC CGC AAG CTT TAC AAG TGC CCA
gln arg thr arg leu ser lys gly asp ile ala gln ala arg lys leu tyr lys cys pro
961 /                                                             991 /                                       331
                                         321
GCC TGT GGA GAG ACC CTG CAA GAC AGC ACA AAC AGC ACA AAC TTC TCC CCT GAA TAC CCC AAT
ala cys gly glu thr leu gln asp ser thr gly asn phe ser ser pro glu tyr pro asn
```

FIG. 6B

```
1021 /  341
GGC TAC TCT GCT CAC ATG CAC TGC GTG TGG CGC ATC TCT GTC ACA CCC GGG GAG AAG ATC
gly tyr ser ala his met his cys val trp arg ile ser val thr pro gly glu lys ile
1081 /  361                                   1111 /  371
ATC CTG AAC TTC ACG TCC CTG GAC CTG TAC CGC AGC CGC CTG TGC TGG TAC GAC TAT GTG
ile leu asn phe thr ser leu asp leu tyr arg ser arg leu cys trp tyr asp tyr val
1141 /  381
GAG GTC CGA GAT GGC TTC TGG AGG AAG GCG CCC CTC CGA GGC CGC TTC TGC GGG TCC AAA
glu val arg asp gly phe trp arg lys ala pro leu arg gly arg phe cys gly ser lys
1201 /  401
CTC CCT GAG CCT ATC GTC TCC ACT GAC AGC CGC CTC TGG GTT GAA TTC CGC AGC AGC AGC
leu pro glu pro ile val ser thr asp ser arg leu trp val glu phe arg ser ser ser
1261 /  421
AAT TGG GTT GGA AAG GGC TTC TTT GCA GTC TAC GAA GCC ATC TGC GGG GGT GAT GTG AAA
asn trp val gly lys gly phe phe ala val tyr glu ala ile cys gly gly asp val lys
1321 /  441                                   1351 /  451
AAG GAC TAT GGC CAC ATT CAA TCG CCC AAC TAC CCA GAC GAT TAC CGG CCC AGC AAA GTC
lys asp tyr gly his ile gln ser pro asn tyr pro asp asp tyr arg pro ser lys val
1381 /  461                                   1411 /  471
TGC ATC TGG CGG ATC CAG GTG TCT GAG GGC TTC CAC GTG GGC CTC ACA TTC CAG TCC TTT
cys ile trp arg ile gln val ser glu gly phe his val gly leu thr phe gln ser phe
1441 /  481                                   1471 /  491
GAG ATT GAG CGC CAC GAC AGC TGT GCC TAC TAT CTG GAG GTG CGC GAC GGG CAC AGT
glu ile glu arg his asp ser cys ala tyr tyr leu glu val arg asp gly his ser
1501 /  501                                   1531 /  511
GAG AGC ACC CTC ATC GGG CGC TAC TGT CGC TAC GAG AAG CCT GAT GAC ATC AAG AGC
glu ser ser thr leu ile gly arg tyr cys arg tyr glu lys pro asp asp ile lys ser
```

FIG. 6C

```
1561 /        1591 /
521           531
ACG TCC AGC CGC CTC TGG CTC AAG TTC GTC TCT GAC GGG TCC ATT AAC AAA GCG GGC TTT
thr ser ser arg leu trp leu lys phe val ser asp gly ser ile asn lys ala gly phe
1621 /        1651 /
541           551
GCC GTC AAC TTT TTC AAA GAG GTG GAC GAG TGC TCT CGG CCC AAC CGC GGG GGC TGT GAG
ala val asn phe phe lys glu val asp glu cys ser arg pro asn arg gly gly cys glu
1681 /        1711 /
561           571
CAG CGG TGC CTC AAC ACC CTG GGC AGC TAC AAG TGC AGC TGT GAC CCC GGG TAC GAG CTG
gln arg cys leu asn thr leu gly ser tyr lys cys ser cys asp pro gly tyr glu leu
1741 /        1771 /
581           591
GCC GAC AAG CGC TGT GAG GCT GCT GCA CGC GGA TTC CTC ACC AAG CTC AAC GGC
ala asp lys arg cys glu ala ala ala cys gly gly phe leu thr lys leu asn gly
1801 /        1831 /
601           611
TCC ATC ACC AGC CCG GGC TGG CCC AAG GAG TAC CCC AAC TGC ATC TGG CAG
ser ile thr ser pro gly trp pro lys glu tyr pro pro asn lys asn cys ile trp gln
1861 /        1891 /
621           631
CTG GTG GCC CCC ACC CAG TAC CGC ATC TCC CTG CAG TTT GAC TTC TTT GAG ACA GAG GGC
leu val ala pro thr gln tyr arg ile ser leu gln phe asp phe phe glu thr glu gly
1921 /        1951 /
641           651
AAT GAT GTG TGC AAG TAC GAC TTC GTG GAG GTG CGC AGT GGA CTC ACA GCT GAC TCC AAG
asn asp val cys lys tyr asp phe val glu val arg ser gly leu thr ala asp ser lys
1981 /        2011 /
661           671
CTG CAT GGC AAG TTC TGT GGT TCT GAG AAG CCC GAG GTC ATC ACC TCC CAG TAC AAC AAC
leu his gly lys phe cys gly ser glu lys pro glu val ile thr ser gln tyr asn asn
2041 /        2071 /
681           691
ATG CGC GTG GAG TTC AAG TCC GAC AAC ACC GTG TCC AAA AAG GGC TTC AAG GCC CAC TTC
met arg val glu phe lys ser asp asn thr val ser lys lys gly phe lys ala his phe
```

FIG. 6D

```
2101 /  701                                              2131 /  711
TTC TCA GAA AAC AGG CCA GCT CTG CAG CCC CCT CGG GGA CGC CCC CAC CAG CTC AAA TTC
phe ser glu asn arg pro ala leu gln pro pro arg gly arg pro his gln leu lys phe
2161 /  721                                              2191 /  731
CGA GTG CAG AAA AGA AAC CGG ACC CCC CAG TGA GGC CTG CCA GGC CTC CCG GAC CCC TTG
arg val gln lys arg asn arg thr pro gln OPA
2221 /  741                                              2251 /  751
TTA CTC AGG AAC CTC ACC TTG GAC GGA ATG GGG CTT CGG TGC CCA CCA ACC CCC 2281 /  761                                              2311 /  771
CAC CTC CAC TCT GCC ATT CCG GCC CAC CTC CCT CTG GCC GGA CAG AAC TGG TGC TCT CTT 2341 /  781                                              2371 /  791
CTC CCC ACT GTG CCC GTC CGC GGA CCG GGG ACC CTT CCC CGT GCC CTA CCC CCT CCC ATT 2401 /  801                                              2431 /  811
TTG ATG GTG TCT GTG ACA TTT CCT GTT GTG ACA TTT CCT GTT GTG AAG TAA AAG AGG GAC CCC TGC GTC CTG
```

FIG. 6E

PCP-2 -> 1-phase Translation

DNA sequence   3546 b.p.   ATGCCCGGCGTG ... ACCGAAAGTGTT   linear

```
1      /    1                              31     /   11
ATG CCC GGC GTG GCC CGC CTG CCG CTG CTG GGG CTG CTC CTG CCG CGT CCC GGC
met pro gly val ala arg leu pro leu leu gly leu leu leu pro arg pro gly
61     /   21                              91     /   31
CGG CCG CTG GAC TTG GCC GAC TAC ACC TAT GAC CTG GCG GAG GAC GAC TCG GAG CCC
arg pro leu asp leu ala asp tyr thr tyr asp leu ala glu asp asp ser glu pro
121    /   41                              151    /   51
CTC AAC TAC AAA GAC CCC TGC AAG GCG GCT CTT GGG GAC ATT GCC CTG GAC GAA
leu asn tyr lys asp pro cys lys ala ala phe gly asp ile ala leu asp glu
181    /   61                              211    /   71
GAG GAC CTG AGG GCC TTC CAG GTA CAG GCT GTG GAT CTC AGA CGG CAC ACA GCT CGT
glu asp leu arg ala phe gln val gln ala val asp leu arg arg his thr ala arg
241    /   81                              271    /   91
AAG TCC TCC ATC AAA GCT GCA GTT CCA GGA AAC ACT TCT ACC CCC AGC TGC CAG AGC ACC
lys ser ser ile lys ala ala val pro gly asn thr ser thr pro ser cys gln ser thr
301    /  101                              331    /  111
AAC GGG CAG CCT CGA CCA GAG TCC TGG AGA GGT AGA TCC CGT AGC CGG CGG
asn gly gln pro arg pro glu ser trp arg gly arg trp arg ser arg arg arg
361    /  121                              391    /  131
GCG ACG ACG TCC CGA TCC CGA CCG GAG CCC GAT GGG GTC ATC CCC TTT GTC ATT GGG
ala thr thr ser arg ser arg pro glu gly pro asp gly val ile pro phe val ile gly
421    /  141                              451    /  151
GGA AAC TTC ACT GGT AGC CAG AGG CAG GCA GTC CGG CAG GCC ATG AGG CAC TGG GAG AAG
gly asn phe thr gly ser gln arg gln ala val arg gln ala met arg his trp glu lys
```

FIG. 7A

```
481 /  161
CAC ACC TGT GTC ACC TTC CTG GAG CGC ACT GAC GAG AGC TAT ATT GTG TTC ACC TAT
his thr cys val thr phe leu glu arg thr asp glu ser tyr ile val phe thr tyr
541 /  181                              571 /  191
CGA CCT TGC GGG TGC TGC TCC TAC GTG GGT CGC CGC GGG GGC GGG CCC CAG GCC TCC
arg pro cys gly cys cys ser tyr val gly arg arg gly gly gly pro gln ala ser
601 /  201                              631 /  211
ATC GGC AAG AAC TGT GAC AAG TTC GGC ATT GTG GTC CAC GAG CTG GGC CAC GTC GGC
ile gly lys asn cys asp lys phe gly ile val val his glu leu gly his val gly
661 /  221                              691 /  231
TTC TGG CAC GAA CAC ACT CGG CCA GAC CGC CAC GTT TCC ATC GTT CGT GAG AAC
phe trp his glu his thr arg pro asp arg his val ser ile val arg glu asn
721 /  241                              751 /  251
ATC CAG CCA GGG CAG GAG TAT AAC TTC CTG AAG ATG GAG CCT CAG GAG GTG TCC CTG
ile gln pro gly gln glu tyr asn phe leu lys met glu pro gln glu val ser leu
781 /  261                              811 /  271
GGG GAG ACC TAT GAC TTC GAC AGC ATC ATG CAT TAC GCT CGG AAC ACA TTC TCC AGG GGC
gly glu thr tyr asp phe asp ser ile met his tyr ala arg asn thr phe ser arg gly
841 /  281                              871 /  291
ATC TTC CTG GAT ACC ATT GTC CCC ATT GTC CTT TAC GTG AAA CCT CCC ATT GGC
ile phe leu asp thr ile val pro ile val tyr glu val lys pro pro ile gly
901 /  301                              931 /  311
CAA AGG ACA CGG CTC AGC AAG GGC GAC ATT GCC CAA GCC CGC AAG CTT TAC AAG TGC CCA
gln arg thr arg leu ser lys gly asp ile ala gln ala arg lys leu tyr lys cys pro
961 /  321                              991 /  331
GCC TGT GGA GAG ACC CTG CAA GAC AGC ACA AAC GGC TTC TCC CCT GAA TAC CCC AAT
ala cys gly glu thr leu gln asp ser thr gly asn phe ser pro glu tyr pro asn
```

FIG. 7B

```
1021 /           341
GGC TAC TCT GCT CAC ATG CAC TGC GTG TGG CGC ATC TCT GTC ACA CCC GGG GAG AAG ATC
gly tyr ser ala his met his cys val trp arg ile ser val thr pro gly glu lys ile
      1081 /           361                           1111 /           371
ATC AAC TTC ACG TCC CTG GAC CTG CGC TAC AGC CGC TGC TAC GAC TAT GTG
ile leu asn phe thr ser leu asp leu arg tyr ser arg cys tyr asp tyr val
      1141 /           381
GAG GTC CGA GAT GGC TTC TGG AGG AAG GCG CCC CTC CGA GGC CGC TTC TGC GGG TCC AAA
glu val arg asp gly phe trp arg lys ala pro leu arg gly arg phe cys gly ser lys
      1201 /           401                           1231 /           411
CTC CCT GAG CCT ATC GTC TCC ACT GAC AGC CGC CTC TGG GTT GAA TTC CGC AGC AGC
leu pro glu pro ile val ser thr asp ser arg leu trp val glu phe arg ser ser
      1261 /           421                           1291 /           431
AAT TGG GTT GGA AAG GGC TTC TTT GCA GTC TAC GAA GCC ATC TGC GGG GGT GAT GTG AAA
asn trp val gly lys gly phe phe ala val tyr glu ala ile cys gly gly asp val lys
      1321 /           441                           1351 /           451
AAG GAC TAT GGC CGC CAC ATT CAA TCG CCC AAC TAC CCA GAC GAT TAC CGG CCC AGC AAA GTC
lys asp tyr gly arg his ile gln ser pro asn tyr pro asp asp tyr arg pro ser lys val
      1381 /           461                           1411 /           471
TGC ATC TGG CGG ATC CAG ATC GAG CAG GTG TCT GAG GGC TTC CAC GTG GGC CTC ACA TTC CAG TCC TTT
cys ile trp arg ile gln ile glu gln val ser glu gly phe his val gly leu thr phe gln ser phe
      1441 /           481                           1471 /           491
GAG ATT GAG CGC CAC GAC AGC AGC TGT GCC TAC GAC TAT CTG GAG GTG CGC GAC GGG CAC AGT
glu ile glu arg his asp ser ser cys ala tyr asp tyr leu glu val arg asp gly his ser
      1501 /           501                           1531 /           511
GAG AGC AGC ACC CTC ATC GGG CGC TAC TGT GGC TAT GAG AAG CCT GAT GAC ATC AAG AGC
glu ser ser thr leu ile gly arg tyr cys gly tyr glu lys pro asp asp ile lys ser
```

FIG. 7C

```
1561 /      521
ACG TCC AGC CGC CTC TGG CTC AAG TTC GTC TCT GAC GGG TCC ATT AAC AAA GCG GGC TTT
thr ser ser arg leu trp leu lys phe val ser asp gly ser ile asn lys ala gly phe
1621 /      541                                      1651 /      551

GCC GTC AAC TTT TTC AAA GAG GTG GAC GAG GTG TCT CGG CCC AAC CGC GGG GGC TGT GAG
ala val asn phe phe lys glu val asp glu val ser arg pro asn arg gly gly cys glu
1681 /      561                                      1711 /      571

CAG CGG TGC CTC AAC ACC CTG GGC AGC TAC AAG TGC AGC TGT GAC CCC GGG TAC GAG CTG
gln arg cys leu asn thr leu gly ser tyr lys cys ser cys asp pro gly tyr glu leu
1741 /      581                                      1771 /      591

GCC GAC AAG CGC CGC GCT GCT GCT GTG TGT GAG GCT GCT GCA GAG TTC CTC ACC AAG AAC GGC
ala asp lys arg arg ala ala ala val cys glu ala ala ala glu phe leu thr lys asn gly
1801 /      601                                      1831 /      611

TCC ATC ACC AGC CCG GGC TGG CCC AAG GAG TAC CCC AAG AAC TGC ATC TGG CAG
ser ile thr ser pro gly trp pro lys glu tyr pro lys asn cys ile trp gln
1861 /      621                                      1891 /      631

CTG GTG GCC CCC ACC CAG TAC CGC ATC CTG CAG TTT GAC TTT TTT GAG ACA GAG GGC
leu val ala pro thr gln tyr arg ile leu gln phe asp phe phe glu thr glu gly
1921 /      641                                      1951 /      651

AAT GAT GTG TGC AAG TTC GAC GTC AGT GGA CTC GCA GTG GTG CGC AGT GGA CTC ACA GCT GAC TCC AAG
asn asp val cys lys phe asp val ser gly leu arg val arg ser gly leu thr ala asp ser lys
1981 /      661                                      2011 /      671

CTG CAT GGC AAG TTC TGT GGT TCT GAG AAG CCC GAG ATC ACC TCC CAG TAC AAC AAC
leu his gly lys phe cys gly ser glu lys pro glu ile thr ser gln tyr asn asn
2041 /      681                                      2071 /      691

ATG CGC GTG GAG TTC AAG TCC GAC AAC ACC GTG TCC AAA AAG GGC TTC AAG GCC CAC TTC
met arg val glu phe lys ser asp asn thr val ser lys lys gly phe lys ala his phe
```

FIG. 7D

```
2101 /  701
TTC TCA GAC AAG GAC GAG TGC TCC AAG GAT AAC GGC GGC TGC CAG CAG GAC TGC GTC AAC
phe ser asp lys asp glu cys ser lys asp asn gly gly cys gln gln asp cys val asn
2161 /  711

ACG TTC GGC AGT TAT GAG TGC CAA TGC CGC AGT GGC TTC GTC CTC CAT GAC AAC AAG CAC
thr phe gly ser tyr glu cys gln cys arg ser gly phe val leu his asp asn lys his
2221 /  731

GAC TGC AAA GAA GCC GGC TGT GAC CAC AAG GTG ACA TCC ACC AGT GGT ACC ATC ACC AGC
asp cys lys glu ala gly cys asp his lys val thr ser thr ser gly thr ile thr ser
2281 /  751

CCC AAC TGG CCT GAC AAG TAT CCC AGC AAG GAG TGC ACG TGG GCC ATC TCC AGC ACC
pro asn trp pro asp lys tyr pro ser lys lys glu cys thr trp ala ile ser ser thr
2341 /  771

CCC GGG CAC CGG GTC AAG CTG ACC TTC ATG GAG ATG GAC ATC GAG TCC CAG CCT GAG TGT
pro gly his arg val lys leu thr phe met glu met asp ile glu ser gln pro glu cys
2401 /  791

GCC TAC GAC CAC CTA GAG GTG TTC GAC GGG CGA GAC GCC AAG GCC CCC GTC CTC GGC CGC
ala tyr asp his leu glu val phe asp gly arg asp ala lys ala pro val leu gly arg
2461 /  811

TTC TGT GGG AGC AAG AAG CCC GAG CCC CTG GCC ACA GGC AGC CGC ATG TTC CTG CGC
phe cys gly ser lys lys pro glu pro val leu ala thr gly ser arg met phe leu arg
2521 /  831

TTC TAC TCA GAT AAC TCG GTC CAG CGA AAG GGC TTC CAG GCC TCC CAC GCC ACA GAG TGC
phe tyr ser asp asn ser val gln arg lys gly phe gln ala ser his ala thr glu cys
2581 /  851

GGG GGC CAG GTA CGG GCA GAC GTG AAG ACC AAG GAC CTT TAC TCC CAC GCC CAG TTT GGC
gly gly gln val arg ala asp val lys thr lys asp leu tyr ser his ala gln phe gly
```

FIG. 7E

```
2641 /  881
GAC AAC AAC TAC CCT GGG GGT GTG GAC TGT GAG TGG GTC ATT GTG GCC GAG GAA GGC TAC
asp asn asn tyr pro gly gly val asp cys glu trp val ile val ala glu glu gly tyr
2701 /  901                              2671 /  891
GGC GTG GAG CTC GTG TTC CAG ACC TTT GAG GTG GAG GAG ACC GAC GAG TGC GGC TAT GAC
gly val glu leu val phe gln thr phe glu val glu glu thr asp glu cys gly tyr asp
2761 /  921                              2731 /  911
TAC ATG GAG CTC TTC GAC GGC TAC GAC AGC CCC AGG CTG GGG CGC TAC TGT GGC
tyr met glu leu phe asp gly tyr asp ser pro arg leu gly arg tyr cys gly
2821 /  941                              2791 /  931
TCA GGG CCT CCT GAG GAG TAC TCG GCG GAT TCT GTC CTG GTG AAG TTC CAC TCG
ser gly pro pro glu glu tyr ser ala asp ser val leu val lys phe his ser
2881 /  961                              2851 /  951
GAT GAC ACC ATC ACC AAA AAA GGT TTC CAC CTG CGA TAC AGC ACC AAG TTC CAG GAC
asp asp thr ile thr lys lys gly phe his leu arg tyr ser thr lys phe gln asp
2941 /  981                              2911 /  971
ACA CTC CAC AGC AGG AAG TGA CCA CTG CCT GAG CAG CGG GGA CTG GAG CCT GCT GCC
thr leu his ser arg lys OPA pro leu pro glu gln arg gly leu glu pro ala ala
3001 / 1001                              2971 /  991
CTT GGT CGC CTA GAC CTG ATA GTG TGG ATA GTG GGG CCA ACG CAA CGC ATC CCT CCC
leu gly arg leu asp leu ile val trp ile val gly gly thr gln arg ile pro pro
3061 / 1021                              3031 / 1011
CAG GCC CCA GGA CCT GCA GGG CCA ATG GCC TGG TGA GAC TGT CCA TAG GAG GTG GGG GAA
gln ala pro gly pro ala gly pro met ala trp OPA
3121 / 1041                              3091 / 1031
CTG GAC TCC GGC ATA AGC CAC CAC TTC CCC ACA AAC CCC CAG CAA GGG GCT GGG GCC AGG
                                         3151 / 1051
```

FIG. 7F

```
3181 / 1061                                3211 / 1071
GAG CAG AGC TTC CAC AAG ACA TTT CGA AGT CAT CAT TCC TCT CTT AGG GGG CCC TGC CTG
3241 / 1081                                3271 / 1091
GTG GCA AGA GGG AAT GTC AGC AGG ACC CCA TCC CTG TGT CTC TAC ACG CTG TAT
3301 / 1101                                3331 / 1111
TGT GTA TCA CCG GGG GCA TTA TTT TCA TAA TGT TCA TTT CCC ACC CCT GCT CCA GCC
3361 / 1121                                3391 / 1131
TCG ATT TGG TTT TAT TTT GAG CCC CCA TTC CAC CAC AGT TTC CTG GGG CAC AAG TGT CTG
3421 / 1141                                3451 / 1151
TGC ATG TCC CCC AGG AGC CAC CGT GGG GAG CCG ATG GGG AGG GGA TGG AGA AAC AAG ACA
3481 / 1161                                3511 / 1171
GGG CTT CTC TCA GCC CAT GGC CGG TCA GCC ACA CCA GGG CAC CGC AGC CAA TAA ACC GAA
3541 / 1181
AGT GTT
```

FIG. 7G

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
        (A) LENGTH: 2457 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..2190

(xi) SEQUENCE DESCRIPTION: SEQ ID NO: 1:

```
ATG CCC GGC GTG GCC CGC CTG CCG CTG CTG CTC GGG CTG CTG CTG CTC        48
Met Pro Gly Val Ala Arg Leu Pro Leu Leu Leu Gly Leu Leu Leu Leu
 1               5                  10                  15

CCG CGT CCC GGC CGC CCG CTG GAC TTG GCC GAC TAC ACC TAT GAC CTG        96
Pro Arg Pro Gly Arg Pro Leu Asp Leu Ala Asp Tyr Thr Tyr Asp Leu
                20                  25                  30

GCG GAG GAC GAC GAC TCG GAG CCC CTC AAC TAC AAA GAC CCC TGC AAG       144
Ala Glu Asp Asp Asp Ser Glu Pro Leu Asn Tyr Lys Asp Pro Cys Lys
            35                  40                  45

GCG GCT GCC TTT CTT GGG GAC ATT GCC CTG GAC GAA GAG GAC CTG AGG       192
Ala Ala Ala Phe Leu Gly Asp Ile Ala Leu Asp Glu Glu Asp Leu Arg
        50                  55                  60

GCC TTC CAG CTA CAG CAG GCT GTG GAT CTC AGA CGG CAC ACA GCT CGT       240
Ala Phe Gln Leu Gln Gln Ala Val Asp Leu Arg Arg His Thr Ala Arg
 65                  70                  75                  80

AAG TCC TCC ATC AAA GCT GCA GTT CCA GGA AAC ACT TCT ACC CCC AGC       288
Lys Ser Ser Ile Lys Ala Ala Val Pro Gly Asn Thr Ser Thr Pro Ser
                85                  90                  95

TGC CAG AGC ACC AAC GGG CAG CCT CAG AGG GGA CCC TGT GGG AGA TGG       336
Cys Gln Ser Thr Asn Gly Gln Pro Gln Arg Gly Pro Cys Gly Arg Trp
               100                 105                 110
```

```
AGA GGT AGA TCC CGT AGC CGG CGG GCG GCG ACG TCC CGA CCA GAG CGT        384
Arg Gly Arg Ser Arg Ser Arg Arg Ala Ala Thr Ser Arg Pro Glu Arg
            115                 120                 125

GTG TGG CCC GAT GGG GTC ATC CCC TTT GTC ATT GGG GGA AAC TTC ACT        432
Val Trp Pro Asp Gly Val Ile Pro Phe Val Ile Gly Gly Asn Phe Thr
    130                 135                 140

GGT AGC CAG AGG GCA GTC TTC CGG CAG GCC ATG AGG CAC TGG GAG AAG        480
Gly Ser Gln Arg Ala Val Phe Arg Gln Ala Met Arg His Trp Glu Lys
145                 150                 155                 160

CAC ACC TGT GTC ACC TTC CTG GAG CGC ACT GAC GAG CAC AGC TAT ATT        528
His Thr Cys Val Thr Phe Leu Glu Arg Thr Asp Glu His Ser Tyr Ile
                165                 170                 175

CTG TTC ACC TAT CGA CCT TGC GGG TGC TGC TCC TAC GTG GGT CCC CGC        576
Leu Phe Thr Tyr Arg Pro Cys Gly Cys Cys Ser Tyr Val Gly Pro Arg
            180                 185                 190

GGC GGG GGG CCC CAG GCC ATC TCC ATC GGC AAG AAC TGT GAC AAG TTC        624
Gly Gly Gly Pro Gln Ala Ile Ser Ile Gly Lys Asn Cys Asp Lys Phe
        195                 200                 205

GGG ATT GTG GTC CAC GAG CTG GGC CAC GTC GTC GGG TTC TGG CAC GAA        672
Gly Ile Val Val His Glu Leu Gly His Val Val Gly Phe Trp His Glu
    210                 215                 220

CAC ACT CGG CCA GAC CGG GAC CGC CAC GTT TCC ATC GTT CGT GAG AAC        720
His Thr Arg Pro Asp Arg Asp Arg His Val Ser Ile Val Arg Glu Asn
225                 230                 235                 240

ATC CAG CCA GGG CAG GAG TAT AAC TTC CTG AAG ATG GAG CCT CAG GAG        768
Ile Gln Pro Gly Gln Glu Tyr Asn Phe Leu Lys Met Glu Pro Gln Glu
                245                 250                 255

GTG GAG TCC CTG GGG GAG ACC TAT GAC TTC GAC AGC ATC ATG CAT TAC        816
Val Glu Ser Leu Gly Glu Thr Tyr Asp Phe Asp Ser Ile Met His Tyr
            260                 265                 270

GCT CGG AAC ACA TTC TCC AGG GGC ATC TTC CTG GAT ACC ATT GTC CCC        864
Ala Arg Asn Thr Phe Ser Arg Gly Ile Phe Leu Asp Thr Ile Val Pro
        275                 280                 285

AAG TAT GAG GTG AAC GGG GTG AAA CCT CCC ATT GGC CAA AGG ACA CGG        912
Lys Tyr Glu Val Asn Gly Val Lys Pro Pro Ile Gly Gln Arg Thr Arg
    290                 295                 300

CTC AGC AAG GGG GAC ATT GCC CAA GCC CGC AAG CTT TAC AAG TGC CCA        960
Leu Ser Lys Gly Asp Ile Ala Gln Ala Arg Lys Leu Tyr Lys Cys Pro
305                 310                 315                 320

GCC TGT GGA GAG ACC CTG CAA GAC AGC ACA GGC AAC TTC TCC TCC CCT       1008
Ala Cys Gly Glu Thr Leu Gln Asp Ser Thr Gly Asn Phe Ser Ser Pro
                325                 330                 335

GAA TAC CCC AAT GGC TAC TCT GCT CAC ATG CAC TGC GTG TGG CGC ATC       1056
Glu Tyr Pro Asn Gly Tyr Ser Ala His Met His Cys Val Trp Arg Ile
            340                 345                 350

TCT GTC ACA CCC GGG GAG AAG ATC ATC CTG AAC TTC ACG TCC CTG GAC       1104
Ser Val Thr Pro Gly Glu Lys Ile Ile Leu Asn Phe Thr Ser Leu Asp
        355                 360                 365

CTG TAC CGC AGC CCC CTG TGC TGG TAC GAC TAT GTG GAG GTC CGA GAT       1152
Leu Tyr Arg Ser Pro Leu Cys Trp Tyr Asp Tyr Val Glu Val Arg Asp
    370                 375                 380

GGC TTC TGG AGG AAG GCG CCC CTC CGA GGG CGC TTC TGC GGG TCC AAA       1200
Gly Phe Trp Arg Lys Ala Pro Leu Arg Gly Arg Phe Cys Gly Ser Lys
385                 390                 395                 400

CTC CCT GAG CCT ATC GTC TCG ACT GAC AGC CGC CTC TGG GTT GAA TTC       1248
Leu Pro Glu Pro Ile Val Ser Thr Asp Ser Arg Leu Trp Val Glu Phe
                405                 410                 415

CGC AGC AGC AGC AAT TGG GTT GGA AAC GGC TTC TTT GCA GTC TAC GAA       1296
Arg Ser Ser Ser Asn Trp Val Gly Asn Gly Phe Phe Ala Val Tyr Glu
            420                 425                 430
```

```
GGG ATC TGC GGG GGT GAT GTG AAA AAG GAC TAT GGG CAC ATT CAA TCG    1344
Gly Ile Cys Gly Gly Asp Val Lys Lys Asp Tyr Gly His Ile Gln Ser
            435                 440                 445

CCC AAC TAC CCA GAC GAT TAC CGG CCC AGC AAA GTC TGC ATC TGG CGG    1392
Pro Asn Tyr Pro Asp Asp Tyr Arg Pro Ser Lys Val Cys Ile Trp Arg
            450                 455                 460

ATC CAG GTG TCT GAG GGC TTC CAC GTG GGC CTC ACA TTC CAG TCC TTT    1440
Ile Gln Val Ser Glu Gly Phe His Val Gly Leu Thr Phe Gln Ser Phe
465                 470                 475                 480

GAG ATT GAG CGC CAC GAC AGC TGT GCC TAC GAC TAT CTG GAG GTG CGC    1488
Glu Ile Glu Arg His Asp Ser Cys Ala Tyr Asp Tyr Leu Glu Val Arg
                    485                 490                 495

GAC GGG CAC AGT GAG AGC AGC ACC CTC ATC GGG CGC TAC TGT GGC TAT    1536
Asp Gly His Ser Glu Ser Ser Thr Leu Ile Gly Arg Tyr Cys Gly Tyr
            500                 505                 510

GAG AAG CCT GAT GAC ATC AAG AGC ACG TCC AGC CGC CTC TGG CTC AAG    1584
Glu Lys Pro Asp Asp Ile Lys Ser Thr Ser Ser Arg Leu Trp Leu Lys
            515                 520                 525

TTC GTC TCT GAC GGG TCC ATT AAC AAA GCG GGC TTT GCC GTC AAC TTT    1632
Phe Val Ser Asp Gly Ser Ile Asn Lys Ala Gly Phe Ala Val Asn Phe
            530                 535                 540

TTC AAA GAG GTG GAC GAG TGC TCT CGG CCC AAC CGC GGG GGC TGT GAG    1680
Phe Lys Glu Val Asp Glu Cys Ser Arg Pro Asn Arg Gly Gly Cys Glu
545                 550                 555                 560

CAG CGG TGC CTC AAC ACC CTG GGC AGC TAC AAG TGC AGC TGT CAC CCC    1728
Gln Arg Cys Leu Asn Thr Leu Gly Ser Tyr Lys Cys Ser Cys His Pro
                    565                 570                 575

GGG TAC GAG CTG GCC CCA GAC AAG CGC CGC TGT GAG GCT GCT TGT GGC    1776
Gly Tyr Glu Leu Ala Pro Asp Lys Arg Arg Cys Glu Ala Ala Cys Gly
            580                 585                 590

GGA TTC CTC ACC AAG CTC AAC GGC TCC ATC ACC AGC CCG GGC TGG CCC    1824
Gly Phe Leu Thr Lys Leu Asn Gly Ser Ile Thr Ser Pro Gly Trp Pro
            595                 600                 605

AAG GAG TAC CCC CCC AAC AAG AAC TGC ATC TGG CAG CTG GTG GCC CCC    1872
Lys Glu Tyr Pro Pro Asn Lys Asn Cys Ile Trp Gln Leu Val Ala Pro
            610                 615                 620

ACC CAG TAC CGC ATC TCC CTG CAG TTT GAC TTC TTT GAG ACA GAG GGC    1920
Thr Gln Tyr Arg Ile Ser Leu Gln Phe Asp Phe Phe Glu Thr Glu Gly
625                 630                 635                 640

AAT GAT GTG TGC AAG TAC GAC TTC GTG GAG GTG CGC AGT GGA CTC ACA    1968
Asn Asp Val Cys Lys Tyr Asp Phe Val Glu Val Arg Ser Gly Leu Thr
                    645                 650                 655

GCT CAC TCC AAG CTG CAT GGC AAG TTC TGT GGT TCT GAG AAG CCC GAG    2016
Ala His Ser Lys Leu His Gly Lys Phe Cys Gly Ser Glu Lys Pro Glu
            660                 665                 670

GTC ATC ACC TCC CAG TAC AAC AAC ATG CGC GTG GAG TTC AAG TCC GAC    2064
Val Ile Thr Ser Gln Tyr Asn Asn Met Arg Val Glu Phe Lys Ser Asp
            675                 680                 685

AAC ACC GTG TCC AAA AAG GGC TTC AAG GCC CAC TTC TTC TCA GAA AAC    2112
Asn Thr Val Ser Lys Lys Gly Phe Lys Ala His Phe Phe Ser Glu Asn
            690                 695                 700

AGG CCA GCT CTG CAG CCC CCT CGG GGA CCC CCC CAC CAG CTC AAA TTC    2160
Arg Pro Ala Leu Gln Pro Pro Arg Gly Pro Pro His Gln Leu Lys Phe
705                 710                 715                 720

CGA GTC CAG AAA AGA AAC CGG ACC CCC CAG TGAGGCCTGC CAGGCCTCCC      2210
Arg Val Gln Lys Arg Asn Arg Thr Pro Gln
                    725                 730

GGACCCCTTG TTACTCAGGA ACCTCACCTT GGACGGAATG GGATGGGGGC TTCGGTGCCC  2270
```

-continued

```
ACCAACCCCC CACCTCCACT CTGCCATTCC GGCCCACCTC CCTCTGGCCG GACAGAACTG    2330

GTGCTCTCTT CTCCCCACTG TGCCCGTCCG CGGACCGGGG ACCCTTCCCC GTGCCCTACC    2390

CCCTCCCATT TTGATGGTGT CTGTGACATT TCCTGTTGTG AAGTAAAAGA GGGACCCCTG    2450

CGTCCTG                                                              2457
```

(2) INFORMATION FOR SEQ ID NO: 2:

(i) SEQUENCE CHARACTERISTICS:
        (A) LENGTH: 730 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Pro Gly Val Ala Arg Leu Pro Leu Leu Gly Leu Leu Leu Leu
 1               5                  10                  15

Pro Arg Pro Gly Arg Pro Leu Asp Leu Ala Asp Tyr Thr Tyr Asp Leu
                20                  25                  30

Ala Glu Asp Asp Ser Glu Pro Leu Asn Tyr Lys Asp Pro Cys Lys
            35                  40                  45

Ala Ala Ala Phe Leu Gly Asp Ile Ala Leu Asp Glu Glu Asp Leu Arg
        50                  55                  60

Ala Phe Gln Leu Gln Gln Ala Val Asp Leu Arg Arg His Thr Ala Arg
 65                  70                  75                  80

Lys Ser Ser Ile Lys Ala Ala Val Pro Gly Asn Thr Ser Thr Pro Ser
                85                  90                  95

Cys Gln Ser Thr Asn Gly Gln Pro Gln Arg Gly Pro Cys Gly Arg Trp
                100                 105                 110

Arg Gly Arg Ser Arg Ser Arg Arg Ala Ala Thr Ser Arg Pro Glu Arg
            115                 120                 125

Val Trp Pro Asp Gly Val Ile Pro Phe Val Ile Gly Gly Asn Phe Thr
            130                 135                 140

Gly Ser Gln Arg Ala Val Phe Arg Gln Ala Met Arg His Trp Glu Lys
145                 150                 155                 160

His Thr Cys Val Thr Phe Leu Glu Arg Thr Asp Glu His Ser Tyr Ile
                165                 170                 175

Leu Phe Thr Tyr Arg Pro Cys Gly Cys Cys Ser Tyr Val Gly Pro Arg
            180                 185                 190

Gly Gly Gly Pro Gln Ala Ile Ser Ile Gly Lys Asn Cys Asp Lys Phe
        195                 200                 205

Gly Ile Val Val His Glu Leu Gly His Val Val Gly Phe Trp His Glu
    210                 215                 220

His Thr Arg Pro Asp Arg Asp Arg His Val Ser Ile Val Arg Glu Asn
225                 230                 235                 240

Ile Gln Pro Gly Gln Glu Tyr Asn Phe Leu Lys Met Glu Pro Gln Glu
                245                 250                 255

Val Glu Ser Leu Gly Glu Thr Tyr Asp Phe Asp Ser Ile Met His Tyr
            260                 265                 270

Ala Arg Asn Thr Phe Ser Arg Gly Ile Phe Leu Asp Thr Ile Val Pro
        275                 280                 285

Lys Tyr Glu Val Asn Gly Val Lys Pro Pro Ile Gly Gln Arg Thr Arg
    290                 295                 300

Leu Ser Lys Gly Asp Ile Ala Gln Ala Arg Lys Leu Tyr Lys Cys Pro
305                 310                 315                 320
```

```
Ala Cys Gly Glu Thr Leu Gln Asp Ser Thr Gly Asn Phe Ser Ser Pro
            325                 330                 335

Glu Tyr Pro Asn Gly Tyr Ser Ala His Met His Cys Val Trp Arg Ile
            340                 345                 350

Ser Val Thr Pro Gly Glu Lys Ile Ile Leu Asn Phe Thr Ser Leu Asp
            355                 360                 365

Leu Tyr Arg Ser Pro Leu Cys Trp Tyr Asp Tyr Val Glu Val Arg Asp
        370                 375                 380

Gly Phe Trp Arg Lys Ala Pro Leu Arg Gly Arg Phe Cys Gly Ser Lys
385                 390                 395                 400

Leu Pro Glu Pro Ile Val Ser Thr Asp Ser Arg Leu Trp Val Glu Phe
                405                 410                 415

Arg Ser Ser Asn Trp Val Gly Asn Gly Phe Phe Ala Val Tyr Glu
                420                 425                 430

Gly Ile Cys Gly Gly Asp Val Lys Lys Asp Tyr Gly His Ile Gln Ser
            435                 440                 445

Pro Asn Tyr Pro Asp Asp Tyr Arg Pro Ser Lys Val Cys Ile Trp Arg
        450                 455                 460

Ile Gln Val Ser Glu Gly Phe His Val Gly Leu Thr Phe Gln Ser Phe
465                 470                 475                 480

Glu Ile Glu Arg His Asp Ser Cys Ala Tyr Asp Tyr Leu Glu Val Arg
                485                 490                 495

Asp Gly His Ser Glu Ser Ser Thr Leu Ile Gly Arg Tyr Cys Gly Tyr
            500                 505                 510

Glu Lys Pro Asp Asp Ile Lys Ser Thr Ser Ser Arg Leu Trp Leu Lys
        515                 520                 525

Phe Val Ser Asp Gly Ser Ile Asn Lys Ala Gly Phe Ala Val Asn Phe
    530                 535                 540

Phe Lys Glu Val Asp Glu Cys Ser Arg Pro Asn Arg Gly Gly Cys Glu
545                 550                 555                 560

Gln Arg Cys Leu Asn Thr Leu Gly Ser Tyr Lys Cys Ser Cys His Pro
                565                 570                 575

Gly Tyr Glu Leu Ala Pro Asp Lys Arg Arg Cys Glu Ala Ala Cys Gly
            580                 585                 590

Gly Phe Leu Thr Lys Leu Asn Gly Ser Ile Thr Ser Pro Gly Trp Pro
        595                 600                 605

Lys Glu Tyr Pro Pro Asn Lys Asn Cys Ile Trp Gln Leu Val Ala Pro
    610                 615                 620

Thr Gln Tyr Arg Ile Ser Leu Gln Phe Asp Phe Phe Glu Thr Glu Gly
625                 630                 635                 640

Asn Asp Val Cys Lys Tyr Asp Phe Val Glu Val Arg Ser Gly Leu Thr
                645                 650                 655

Ala His Ser Lys Leu His Gly Lys Phe Cys Gly Ser Glu Lys Pro Glu
            660                 665                 670

Val Ile Thr Ser Gln Tyr Asn Asn Met Arg Val Glu Phe Lys Ser Asp
        675                 680                 685

Asn Thr Val Ser Lys Lys Gly Phe Lys Ala His Phe Phe Ser Glu Asn
    690                 695                 700

Arg Pro Ala Leu Gln Pro Pro Arg Gly Pro Pro His Gln Leu Lys Phe
705                 710                 715                 720

Arg Val Gln Lys Arg Asn Arg Thr Pro Gln
                725                 730
```

(2) INFORMATION FOR SEQ ID NO: 3:

(i) SEQUENCE CHARACTERISTICS:
        (A) LENGTH: 3546 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..2958

(xi) SEQUENCE DESCRIPTION: SEQ ID NO: 3:

```
ATG CCC GGC GTG GCC CGC CTG CCG CTG CTC GGG CTG CTG CTG CCC         48
Met Pro Gly Val Ala Arg Leu Pro Leu Leu Gly Leu Leu Leu Pro
            735                 740                 745

CCG CGT CCC GGC CGG CCG CTG GAC TTC CCC GAC TAC ACC TAT GAC CTG     96
Pro Arg Pro Gly Arg Pro Leu Asp Phe Pro Asp Tyr Thr Tyr Asp Leu
                750                 755                 760

GCG GAG GAG GAC GAC TCG GAG CCC CTC AAC TAC AAA GAC CCC TGC AAG    144
Ala Glu Glu Asp Asp Ser Glu Pro Leu Asn Tyr Lys Asp Pro Cys Lys
            765                 770                 775

GCG GCT GCC TTT CTT GGG GAC ATT GCC CTG GAC GAA GAG GAC CTG AGG    192
Ala Ala Ala Phe Leu Gly Asp Ile Ala Leu Asp Glu Glu Asp Leu Arg
            780                 785                 790

GCC TTC CAG GTA CAG CAG GCT GTG GAT GTC AGA CGG CAC ACA GCT CGT    240
Ala Phe Gln Val Gln Gln Ala Val Asp Val Arg Arg His Thr Ala Arg
795                 800                 805                 810

AAG TCC TCC ATC AAA GCT GCA GTT CCA GGA AAC ACT TCT ACC CCC ACC    288
Lys Ser Ser Ile Lys Ala Ala Val Pro Gly Asn Thr Ser Thr Pro Thr
                815                 820                 825

TGC CAG AGC ACC AAC GGG CAG CCT CAG AGG GGA GCC TGT GGG AGA TGG    336
Cys Gln Ser Thr Asn Gly Gln Pro Gln Arg Gly Ala Cys Gly Arg Trp
            830                 835                 840

AGA GGT AGA TCC CGT AGC CGG CGG GCG GCG ACG TCC CGA CCA GAG CCT    384
Arg Gly Arg Ser Arg Ser Arg Arg Ala Ala Thr Ser Arg Pro Glu Pro
            845                 850                 855

GTG TGG CCC GAT GGG GTC ATC CCC TTT GTC ATT GGG GGA AAC TTC ACT    432
Val Trp Pro Asp Gly Val Ile Pro Phe Val Ile Gly Gly Asn Phe Thr
860                 865                 870

GGT AGC CAG AGG GCA GTC TTC CGG CAG GCC ATG AGG CAC TGG GAG AAG    480
Gly Ser Gln Arg Ala Val Phe Pro Gln Ala Met Arg His Trp Glu Lys
875                 880                 885                 890

CAC ACC TGT GTG ACC TTC CTG GAG CGC ACT GAC GAG GAC AGC TAT ATT    528
His Thr Cys Val Thr Phe Leu Glu Arg Thr Asp Glu Asp Ser Tyr Ile
                895                 900                 905

CTG TTC ACC TAT GCA CCT TGC GGG TGC TGC TCC TAC GTG GGT CGC CGC    576
Leu Phe Thr Tyr Ala Pro Cys Gly Cys Cys Ser Tyr Val Gly Arg Arg
            910                 915                 920

GGG GGG GGG CCC CAG GCC ATC TCC ATG GGC AAG AAC TGT GAC AAG TTC    624
Gly Gly Gly Pro Gln Ala Ile Ser Met Gly Lys Asn Cys Asp Lys Phe
            925                 930                 935

GGG ATT GTG GTC CAC GAG CTG GGC CAC GTC GTC GGC TTG TGG CAC GAA    672
Gly Ile Val Val His Glu Leu Gly His Val Val Gly Leu Trp His Glu
            940                 945                 950

CAC ACT GGG CCA GAC CGG GAC CGC CAG GTT TCC ATC GTT CGT GAG AAC    720
His Thr Gly Pro Asp Arg Asp Arg Gln Val Ser Ile Val Arg Glu Asn
955                 960                 965                 970

ATC CAG CCA GGG CAG GAG TAT AAC TTC CTG AAG ATG GAG CCT CAG GAG    768
Ile Gln Pro Gly Gln Glu Tyr Asn Phe Leu Lys Met Glu Pro Gln Glu
```

-continued

```
                        975                 980                 985
GTG GAG TCC CTG GGG GAG ACC TAT GAC TTC GAC AGC ATC ATG CAT TAC        816
Val Glu Ser Leu Gly Glu Thr Tyr Asp Phe Asp Ser Ile Met His Tyr
                990                 995                1000

GCT CGG AAC ACA TTC TCC AGG GGC ATC TTC CTG GAT ACC ATT GTC CCC        864
Ala Arg Asn Thr Phe Ser Arg Gly Ile Phe Leu Asp Thr Ile Val Pro
            1005                1010                1015

AAG TAT GAG GTG AAC GGG GTG AAA CCT CCC ATT GGC CAA AGG ACA CGG        912
Lys Tyr Glu Val Asn Gly Val Lys Pro Pro Ile Gly Gln Arg Thr Arg
        1020                1025                1030

CTC AGG AAG GGG GAC ATT GCC CAA GCC CCC AAG CTT TAC AAG TGC CCA        960
Leu Arg Lys Gly Asp Ile Ala Gln Ala Pro Lys Leu Tyr Lys Cys Pro
1035                1040                1045                1050

GCC TGT GGA GAG ACC CTG CAA GAC AGC ACA GGC AAC TTC TCC TCC CCT       1008
Ala Cys Gly Glu Thr Leu Gln Asp Ser Thr Gly Asn Phe Ser Ser Pro
            1055                1060                1065

GAA TAC CCC AAT GGC TAC TCT GCT CAC ATG CAC TGC GTG TGG CGC ATC       1056
Glu Tyr Pro Asn Gly Tyr Ser Ala His Met His Cys Val Trp Arg Ile
        1070                1075                1080

TGT GTC ACA CCC GGG GAG AAG ATC ATC CTG AAC TTC ACG TCC CTG GAC       1104
Cys Val Thr Pro Gly Glu Lys Ile Ile Leu Asn Phe Thr Ser Leu Asp
    1085                1090                1095

CTG TAC CGC AGC GGC CTG TGC TGG TAC CAG TAT GTG GAG GTC CGA GAT       1152
Leu Tyr Arg Ser Gly Leu Cys Trp Tyr Gln Tyr Val Glu Val Arg Asp
        1100                1105                1110

GGC TTC TGG AGG AAG GCC CCC CTC CGA GGC CGC TTC TGC GGG TCC AAA       1200
Gly Phe Trp Arg Lys Ala Pro Leu Arg Gly Arg Phe Cys Gly Ser Lys
1115                1120                1125                1130

CTG CCT GAG CCT ATC GTC TCC ACT GAC AGC CGC CTC TGG GTT CAA TTC       1248
Leu Pro Glu Pro Ile Val Ser Thr Asp Ser Arg Leu Trp Val Gln Phe
            1135                1140                1145

CGC AGC AGC AGC AAT TGG CTT GGA AAG GGC TTC TTT CCA GTC TAC GAA       1296
Arg Ser Ser Ser Asn Trp Leu Gly Lys Gly Phe Phe Pro Val Tyr Glu
        1150                1155                1160

GCC ATG TGG GGG GGT GAT GTG AAA AAG GAC TAT GGC CAG ATT CAA TCG       1344
Ala Met Trp Gly Gly Asp Val Lys Lys Asp Tyr Gly Gln Ile Gln Ser
    1165                1170                1175

CCC AAC TAC CCA GAC GAT TAC CGG CCC AGC AAA GTG TGG ATG TGG CGG       1392
Pro Asn Tyr Pro Asp Asp Tyr Arg Pro Ser Lys Val Trp Met Trp Arg
        1180                1185                1190

ATC CAG GTG TCT GAG GGC TTC GAC GTG GGC CTC ACA TTC CAG TCC TTT       1440
Ile Gln Val Ser Glu Gly Phe Asp Val Gly Leu Thr Phe Gln Ser Phe
1195                1200                1205                1210

GAG ATT GAG CGC CAC GAC AGC TGT GGG TAC GAC TAT CTG GAG GTG CGC       1488
Glu Ile Glu Arg His Asp Ser Cys Gly Tyr Asp Tyr Leu Glu Val Arg
            1215                1220                1225

GAC GGG CAC AGT GAG AGC AGC ACC CTC ATC GGG CGC TAC TGT CGC TAT       1536
Asp Gly His Ser Glu Ser Ser Thr Leu Ile Gly Arg Tyr Cys Arg Tyr
        1230                1235                1240

GAG AAG CCT GAT GAG ATC AAG AGC ACG TCG AGC CCC CTC TGG CTC AAG       1584
Glu Lys Pro Asp Glu Ile Lys Ser Thr Ser Ser Pro Leu Trp Leu Lys
    1245                1250                1255

TTC GTC TCT GAC GGG TCC ATT AAC AAA CCC GGC TTT GCC GTC AAC TTT       1632
Phe Val Ser Asp Gly Ser Ile Asn Lys Pro Gly Phe Ala Val Asn Phe
        1260                1265                1270

TTC AAA GAG GTC GAC GAG TGC TCT CGG CCC AAC CGC GGG GGG TGT GAG       1680
Phe Lys Glu Val Asp Glu Cys Ser Arg Pro Asn Arg Gly Gly Cys Glu
1275                1280                1285                1290

CAG CGG TGC CTC AAC ACC CTG GGC AGC TAC AAG TGG AGC TGT GAC CCC       1728
```

```
                                                                -continued

Gln Arg Cys Leu Asn Thr Leu Gly Ser Tyr Lys Trp Ser Cys Asp Pro
            1295                1300                1305

GGG TAC GAG CTG CCC CCA GAG AAG CGC CGC TGT GAG GCT CCT TGT GGC      1776
Gly Tyr Glu Leu Pro Pro Glu Lys Arg Arg Cys Glu Ala Pro Cys Gly
1310                1315                1320

GGA TTC CTC ACC AAG CTC AAC GGC TCC ATC AGC AGG GGG GGC TGG CCC      1824
Gly Phe Leu Thr Lys Leu Asn Gly Ser Ile Ser Arg Gly Gly Trp Pro
        1325                1330                1335

AAG GAG TAC CCC CCC AAC AAG AAC TGC ATC TGG CAG CTG GTG GCC CCC      1872
Lys Glu Tyr Pro Pro Asn Lys Asn Cys Ile Trp Gln Leu Val Ala Pro
    1340                1345                1350

ACC CAG TAC CGC ATC TCC CTG CAG TTT GAC TTC TTT GAG ACA GAG GGC      1920
Thr Gln Tyr Arg Ile Ser Leu Gln Phe Asp Phe Phe Glu Thr Glu Gly
1355                1360                1365                1370

AAT GAT GTG TGC AAG TAC GAC TTC GTG GAG GTG CGC AGT GGA CTC ACA      1968
Asn Asp Val Cys Lys Tyr Asp Phe Val Glu Val Arg Ser Gly Leu Thr
        1375                1380                1385

GCT GAC TCC AAG CTG CAT GGC AAG TTC TGT GGT TCT GAG AAG CCC GAG      2016
Ala Asp Ser Lys Leu His Gly Lys Phe Cys Gly Ser Glu Lys Pro Glu
    1390                1395                1400

GTC ATC ACC TCC CAG TAC AAC AAC ATG CGC GTG GAG TTC AAG TCC GAC      2064
Val Ile Thr Ser Gln Tyr Asn Asn Met Arg Val Glu Phe Lys Ser Asp
        1405                1410                1415

AAC ACC GTG TCC AAA AAG GGC TTC AAG GCC CAC TTC TTC TCA GAC AAG      2112
Asn Thr Val Ser Lys Lys Gly Phe Lys Ala His Phe Phe Ser Asp Lys
    1420                1425                1430

GAC GAG TGC TCC AAG GAT AAC GGC GGC TGC CAG CAG GAC TGC GTC AAC      2160
Asp Glu Cys Ser Lys Asp Asn Gly Gly Cys Gln Gln Asp Cys Val Asn
1435                1440                1445                1450

ACG TTC GGC AGT TAT GAG TGC CAA TGC CGC AGT GGC TTC GTC CTC CAT      2208
Thr Phe Gly Ser Tyr Glu Cys Gln Cys Arg Ser Gly Phe Val Leu His
        1455                1460                1465

GAC AAC AAG CAC GAC TGC AAA GAA CCC GGC TGT GAC CAC AAG GTG ACA      2256
Asp Asn Lys His Asp Cys Lys Glu Pro Gly Cys Asp His Lys Val Thr
    1470                1475                1480

TCC ACC AGT GGT ACC ATC ACC AGC CCC AAC TGG CCT GAC AAG TAT CCC      2304
Ser Thr Ser Gly Thr Ile Thr Ser Pro Asn Trp Pro Asp Lys Tyr Pro
        1485                1490                1495

AGC AAG AAG GAG TGC ACC TGG GCC ATC TCC AGC ACC CCC GGG CAC CGG      2352
Ser Lys Lys Glu Cys Thr Trp Ala Ile Ser Ser Thr Pro Gly His Arg
    1500                1505                1510

GTC AAG CTG ACC TTC ATG GAG ATG GAC ATC GAG TCC CAG CCT GAG TGT      2400
Val Lys Leu Thr Phe Met Glu Met Asp Ile Glu Ser Gln Pro Glu Cys
1515                1520                1525                1530

GCC TAC GAC CAC CTA GAG GTG TTC GAC GGG CGA GAC GCC AAG GCC CCC      2448
Ala Tyr Asp His Leu Glu Val Phe Asp Gly Arg Asp Ala Lys Ala Pro
        1535                1540                1545

GTC CTC GGC CGC TTC TGT GGG AGC AAG AAG CCC GAG CCC GTC CTG GGG      2496
Val Leu Gly Arg Phe Cys Gly Ser Lys Lys Pro Glu Pro Val Leu Gly
        1550                1555                1560

ACA GGC AGC CGC ATG TTC CTG CGC TTC TAC TCA GAT AAC TCG GTC CAG      2544
Thr Gly Ser Arg Met Phe Leu Arg Phe Tyr Ser Asp Asn Ser Val Gln
        1565                1570                1575

CGA AAG GGG TTC CAG GCC TCC CAC GCC ACA GAG TGC GGG GGC CAG GTA      2592
Arg Lys Gly Phe Gln Ala Ser His Ala Thr Glu Cys Gly Gly Gln Val
    1580                1585                1590

GGG GCA GAC GTG AAG ACC AAG GAC CTT TAC TCC CAC GCC CAG TTT GGC      2640
Gly Ala Asp Val Lys Thr Lys Asp Leu Tyr Ser His Ala Gln Phe Gly
1595                1600                1605                1610
```

-continued

```
GAC AAC AAC TAC CCT GGG GGT GTG GAC TGT GAG TGG GTC ATT GTG CCC      2688
Asp Asn Asn Tyr Pro Gly Gly Val Asp Cys Glu Trp Val Ile Val Pro
                1615                1620                1625

GAG GAA GGC TAC GGC GTG GAG GTC CTC TTC CAG ACC TTT GAG GTG GAG      2736
Glu Glu Gly Tyr Gly Val Glu Val Leu Phe Gln Thr Phe Glu Val Glu
            1630                1635                1640

GAC CAG ACC GAC TGC GGC TAT CAC TAC ATG GAG CTC TTC GAC GGC TAC      2784
Asp Gln Thr Asp Cys Gly Tyr His Tyr Met Glu Leu Phe Asp Gly Tyr
        1645                1650                1655

GAC AGC ACA GCC CCC AGG CTG GGG CGC TAC TGT GGC TCA GGG CCT CCT      2832
Asp Ser Thr Ala Pro Arg Leu Gly Arg Tyr Cys Gly Ser Gly Pro Pro
    1660                1665                1670

GAG GAG GTG TAC TCG GCG GGA GAT TCT GTC CTG GTG AAG TTC CAC TCG      2880
Glu Glu Val Tyr Ser Ala Gly Asp Ser Val Leu Val Lys Phe His Ser
1675                1680                1685                1690

GAT GAC ACC ATC ACC AAA AAA GGT TTC CAC CTG CGA TAC ACC AGC ACC      2928
Asp Asp Thr Ile Thr Lys Lys Gly Phe His Leu Arg Tyr Thr Ser Thr
                1695                1700                1705

AAG TTC CAG GAC ACA CTC CAC AGC AGG AAG TGACCACTGC CTGAGCAGGG        2978
Lys Phe Gln Asp Thr Leu His Ser Arg Lys
                1710                1715

GCGGGGACTG GAGCCTGCTG CCCTTGGTCG CCTAGACTGG ATAGTGGGGG TGGGCGGAAC    3038

GCAACGCACC ATCCCTCTCC CCCAGGCCCC AGGACCTCCA GCCCCAATGG CCTGGTGAGA    3098

CTGTCCATAG GAGGTGGGGG AACTGGACTC CGGCATAAGC CACTTCCCCA CAAACCCCCA    3158

CCAGCAAGGG GCTGGGGCCA GGGAGCAGAG CTTCCACAAG ACATTTCGAA GTCATCATTC    3218

CTCTCTTAGG GGGCCCTGCC TGCTGGCAAG AGGGAATGTC AGCAGGACCC CATCGCCATC    3278

CCTGTGTCTC TACACGCTCT ATTGTGTATC ACCGGGGGCA TTATTTTCAT TGTAATGTTC    3338

ATTTCCCACC CCTGCTCCAG CCTCGATTTG GTTTTATTTT GAGCCCCCAT TCCACCACAG    3398

TTTCCTGGGG CACAAGTGTC TGTGCATGTC CCCCAGGAGC CACCGTGGGG AGCCGATGGG    3458

GAGGGGATGG AGAAACAAGA CAGGGCTTCT CTCAGCCCAT GGCCGGTCAG CCACACCAGG    3518

GCACCGCAGC CAATAAACCG AAAGTGTT                                      3546
```

(2) INFORMATION FOR SEQ ID NO: 4:

(i) SEQUENCE CHARACTERISTICS:
        (A) LENGTH: 986 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Pro Gly Val Ala Arg Leu Pro Leu Leu Gly Leu Leu Leu Pro
 1               5                  10                  15

Pro Arg Pro Gly Arg Pro Leu Asp Phe Pro Asp Tyr Thr Tyr Asp Leu
                20                  25                  30

Ala Glu Glu Asp Asp Ser Glu Pro Leu Asn Tyr Lys Asp Pro Cys Lys
            35                  40                  45

Ala Ala Ala Phe Leu Gly Asp Ile Ala Leu Asp Glu Glu Asp Leu Arg
    50                  55                  60

Ala Phe Gln Val Gln Gln Ala Val Asp Val Arg Arg His Thr Ala Arg
65                  70                  75                  80

Lys Ser Ser Ile Lys Ala Ala Val Pro Gly Asn Thr Ser Thr Pro Thr
                85                  90                  95

Cys Gln Ser Thr Asn Gly Gln Pro Gln Arg Gly Ala Cys Gly Arg Trp
```

```
                100                 105                 110
Arg Gly Arg Ser Arg Ser Arg Ala Ala Thr Ser Arg Pro Glu Pro
            115                 120                 125
Val Trp Pro Asp Gly Val Ile Pro Phe Val Ile Gly Asn Phe Thr
130                 135                 140
Gly Ser Gln Arg Ala Val Phe Pro Gln Ala Met Arg His Trp Glu Lys
145                 150                 155                 160
His Thr Cys Val Thr Phe Leu Glu Arg Thr Asp Glu Asp Ser Tyr Ile
                165                 170                 175
Leu Phe Thr Tyr Ala Pro Cys Gly Cys Ser Tyr Val Arg Arg
                180                 185                 190
Gly Gly Gly Pro Gln Ala Ile Ser Met Gly Lys Asn Cys Asp Lys Phe
                195                 200                 205
Gly Ile Val Val His Glu Leu Gly His Val Val Gly Leu Trp His Glu
            210                 215                 220
His Thr Gly Pro Asp Arg Asp Arg Gln Val Ser Ile Val Arg Glu Asn
225                 230                 235                 240
Ile Gln Pro Gly Gln Glu Tyr Asn Phe Leu Lys Met Glu Pro Gln Glu
                245                 250                 255
Val Glu Ser Leu Gly Glu Thr Tyr Asp Phe Asp Ser Ile Met His Tyr
            260                 265                 270
Ala Arg Asn Thr Phe Ser Arg Gly Ile Phe Leu Asp Thr Ile Val Pro
            275                 280                 285
Lys Tyr Glu Val Asn Gly Val Lys Pro Pro Ile Gly Gln Arg Thr Arg
            290                 295                 300
Leu Arg Lys Gly Asp Ile Ala Gln Ala Pro Lys Leu Tyr Lys Cys Pro
305                 310                 315                 320
Ala Cys Gly Glu Thr Leu Gln Asp Ser Thr Gly Asn Phe Ser Ser Pro
                325                 330                 335
Glu Tyr Pro Asn Gly Tyr Ser Ala His Met His Cys Val Trp Arg Ile
                340                 345                 350
Cys Val Thr Pro Gly Glu Lys Ile Ile Leu Asn Phe Thr Ser Leu Asp
            355                 360                 365
Leu Tyr Arg Ser Gly Leu Cys Trp Tyr Gln Tyr Val Glu Val Arg Asp
            370                 375                 380
Gly Phe Trp Arg Lys Ala Pro Leu Arg Gly Arg Phe Cys Gly Ser Lys
385                 390                 395                 400
Leu Pro Glu Pro Ile Val Ser Thr Asp Ser Arg Leu Trp Val Gln Phe
                405                 410                 415
Arg Ser Ser Ser Asn Trp Leu Gly Lys Gly Phe Phe Pro Val Tyr Glu
                420                 425                 430
Ala Met Trp Gly Gly Asp Val Lys Lys Asp Tyr Gly Gln Ile Gln Ser
            435                 440                 445
Pro Asn Tyr Pro Asp Asp Tyr Arg Pro Ser Lys Val Trp Met Trp Arg
            450                 455                 460
Ile Gln Val Ser Glu Gly Phe Asp Val Gly Leu Thr Phe Gln Ser Phe
465                 470                 475                 480
Glu Ile Glu Arg His Asp Ser Cys Gly Tyr Asp Tyr Leu Glu Val Arg
                485                 490                 495
Asp Gly His Ser Glu Ser Ser Thr Leu Ile Gly Arg Tyr Cys Arg Tyr
                500                 505                 510
Glu Lys Pro Asp Glu Ile Lys Ser Thr Ser Ser Pro Leu Trp Leu Lys
            515                 520                 525
```

-continued

```
Phe Val Ser Asp Gly Ser Ile Asn Lys Pro Gly Phe Ala Val Asn Phe
    530                 535                 540
Phe Lys Glu Val Asp Glu Cys Ser Arg Pro Asn Arg Gly Gly Cys Glu
545                 550                 555                 560
Gln Arg Cys Leu Asn Thr Leu Gly Ser Tyr Lys Trp Ser Cys Asp Pro
                565                 570                 575
Gly Tyr Glu Leu Pro Pro Glu Lys Arg Arg Cys Glu Ala Pro Cys Gly
            580                 585                 590
Gly Phe Leu Thr Lys Leu Asn Gly Ser Ile Ser Arg Gly Gly Trp Pro
        595                 600                 605
Lys Glu Tyr Pro Pro Asn Lys Asn Cys Ile Trp Gln Leu Val Ala Pro
    610                 615                 620
Thr Gln Tyr Arg Ile Ser Leu Gln Phe Asp Phe Glu Thr Glu Gly
625                 630                 635                 640
Asn Asp Val Cys Lys Tyr Asp Phe Val Glu Val Arg Ser Gly Leu Thr
                645                 650                 655
Ala Asp Ser Lys Leu His Gly Lys Phe Cys Gly Ser Glu Lys Pro Glu
            660                 665                 670
Val Ile Thr Ser Gln Tyr Asn Asn Met Arg Val Glu Phe Lys Ser Asp
        675                 680                 685
Asn Thr Val Ser Lys Lys Gly Phe Lys Ala His Phe Phe Ser Asp Lys
    690                 695                 700
Asp Glu Cys Ser Lys Asp Asn Gly Gly Cys Gln Gln Asp Cys Val Asn
705                 710                 715                 720
Thr Phe Gly Ser Tyr Glu Cys Gln Cys Arg Ser Gly Phe Val Leu His
                725                 730                 735
Asp Asn Lys His Asp Cys Lys Glu Pro Gly Cys Asp His Lys Val Thr
            740                 745                 750
Ser Thr Ser Gly Thr Ile Thr Ser Pro Asn Trp Pro Asp Lys Tyr Pro
        755                 760                 765
Ser Lys Lys Glu Cys Thr Trp Ala Ile Ser Ser Thr Pro Gly His Arg
    770                 775                 780
Val Lys Leu Thr Phe Met Glu Met Asp Ile Glu Ser Gln Pro Glu Cys
785                 790                 795                 800
Ala Tyr Asp His Leu Glu Val Phe Asp Gly Arg Asp Ala Lys Ala Pro
                805                 810                 815
Val Leu Gly Arg Phe Cys Gly Ser Lys Lys Pro Glu Pro Val Leu Gly
            820                 825                 830
Thr Gly Ser Arg Met Phe Leu Arg Phe Tyr Ser Asp Asn Ser Val Gln
        835                 840                 845
Arg Lys Gly Phe Gln Ala Ser His Ala Thr Glu Cys Gly Gly Gln Val
    850                 855                 860
Gly Ala Asp Val Lys Thr Lys Asp Leu Tyr Ser His Ala Gln Phe Gly
865                 870                 875                 880
Asp Asn Asn Tyr Pro Gly Gly Val Asp Cys Glu Trp Val Ile Val Pro
                885                 890                 895
Glu Glu Gly Tyr Gly Val Glu Val Leu Phe Gln Thr Phe Glu Val Glu
            900                 905                 910
Asp Gln Thr Asp Cys Gly Tyr His Tyr Met Glu Leu Phe Asp Gly Tyr
        915                 920                 925
Asp Ser Thr Ala Pro Arg Leu Gly Arg Tyr Cys Gly Ser Gly Pro Pro
    930                 935                 940
```

```
                              -continued

Glu Glu Val Tyr Ser Ala Gly Asp Ser Val Leu Val Lys Phe His Ser
945                 950                 955                 960

Asp Asp Thr Ile Thr Lys Lys Gly Phe His Leu Arg Tyr Thr Ser Thr
                965                 970                 975

Lys Phe Gln Asp Thr Leu His Ser Arg Lys
                980                 985

(2) INFORMATION FOR SEQ ID NO: 5:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO: 5:

ATGACTTCGA CAGCATCATG C                                          21

(2) INFORMATION FOR SEQ ID NO: 6:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO: 6:

CTCCAGATAG TCGTAGGCAC A                                          21
```

RECOMBINANT C-PROTEINASE AND PROCESSES, METHODS AND USES THEREOF

1. STATEMENT OF RELATED CASE

This application is a divisional of U.S. patent application Ser. No. 08/872,757, filed Jun. 10, 1997 now U.S. Pat. No. 6,258,584, which is a divisional of application Ser. No. 08/609,187, filed Mar. 1, 1996 now abandoned, from which applications priority is claimed pursuant to 35 U.S.C. §120, and this application is related to Provisional Patent Application Serial No. 60/002,038, filed Aug. 8, 1995, from which priority is claimed under 35 USC §119(e)(1), and which applications are incorporated herein by reference in their entireties.

2. INTRODUCTION

Collagen is integral to, among other things, the proper formation of connective tissue. Therefore, the over- or under-production of collagen or the production of abnormal collagen (including incorrectly processed collagen) has been linked with numerous connective tissue diseases and disorders. Consequently, control and/or modulation of collagen formation has been the focus of study. These studies include efforts to identify enzymes, including C-proteinase, critical to collagen's proper formation and processing.

The present invention is directed to the isolation and identification of the nucleic acid sequence encoding C-proteinase and the corresponding polypeptide, the recognition of such polypeptide activity, and applications, tools, processes and methods of use thereof.

3. BACKGROUND OF THE INVENTION

Collagen Structure. At present, nineteen types of collagens have been identified. These collagens, including fibrillar collagen types I, II, III, are synthesized as procollagen precursor molecules which contain amino- and carboxy-terminal peptide extensions. These peptide extensions, referred to generally as "pro-regions," are designated as N- and C-propeptides, respectively.

Both the N-propeptide and C-propeptide are typically cleaved upon secretion of the procollagen triple helical precursor molecule from the cell to yield a mature triple helical collagen molecule. Upon cleavage, the "mature" collagen molecule is then capable of associating into highly structured collagen fibers. See e.g., Fessler and Fessler, 1978, Annu. Rev. Biochem. 47:129–162; Bornstein and Traub, 1979, in: The Proteins (eds. Neurath, H. and Hill, R. H.), Academic Press, New York, pp. 412–632; Kivirikko et al., 1984, in: Extracellular Matrix Biochemistry (eds. Piez, K. A. and Reddi, A. H.), Elsevier Science Publishing Co., Inc., New York, pp. 83–118; Prockop and Kivirikko, 1984, N. Engl. J. Med. 311:376–383; Kuhn, 1987, in: Structure and Function of Collagen Types (eds. Mayne, R. and Burgeson, R. E.), Academic Press, Inc., Orlando, Fla., pp. 1–42.

Diseases Associated With The Abnormal Production of Collagen. An array of critical diseases has been associated with the inappropriate or unregulated production of collagen, including pathological fibrosis or scarring, including endocardial sclerosis, idiopathic interstitial fibrosis, interstitial pulmonary fibrosis, perimuscular fibrosis, Symmers' fibrosis, pericentral fibrosis, hepatitis, dermatofibroma, billary cirrhosis, alcoholic cirrhosis, acute pulmonary fibrosis, idiopathic pulmonary fibrosis, acute respiratory distress syndrome, kidney fibrosis/glomerulonephritis, kidney fibrosis/diabetic nephropathy, scleroderma/systemic, scleroderma/local, keloids, hypertrophic scars, severe joint adhesions/arthritis, myelofibrosis, corneal scarring, cystic fibrosis, muscular dystrophy (duchenne's), cardiac fibrosis, muscular fibrosis/retinal separation, esophageal stricture, payronles disease. Further fibrotic disorders may be induced or initiated by surgery, including scar revision/plastic surgeries, glaucoma, cataract fibrosis, corneal scarring, joint adhesions, graft vs. host disease, tendon surgery, nerve entrapment, dupuytren's contracture, OB/GYN adhesions/fibrosis, pelvic adhesions, peridural fibrosis, restenosis.

One strategy for the treatment of these diseases is the inhibition of the pathological overproduction of collagen. The identification and isolation of enzymes involved in the collagen production and processing are therefore of major medical interest to provide for suitable targets for drug development.

Similarly, a strategy for the treatment of diseases resulting from the pathological underproduction of collagen, where the underproduction of collagen is the consequence of improper processing of procollagen, is the administration of C-proteinase.

Background Information Regarding C-Proteinase. C-proteinase is an enzyme that catalyzes the cleavage of the C-propeptide of fibrillar collagens, including type I, type II, and type III collagen. The enzyme was first observed in culture media of human and mouse fibroblasts (Goldberg et al., 1975, Cell 4:45–50; Kessler and Goldberg, 1978, Anal. Biochem. 86:463–469), and chick tendon fibroblasts (Duskin et al., 1978, Arch. Biochem. Biophys. 185:326–332; Leung et al., 1979, J. Biol. Chem. 254:224–232). An acidic proteinase which removes the C-terminal propeptides from type I procollagen has also been identified. Davidson et al., 1979, Eur. J. Biochem. 100:551.

A partially purified protein having C-proteinase activity was obtained from chick calvaria in 1982. Njieha et al., 1982, Biochemistry 23:757–764. In 1985, natural C-proteinase was isolated, purified and characterized from conditioned media of chick embryo tendons. Hojima et al., 1985, J. Biol. Chem. 260:15996–16003. Murine C-proteinase has been subsequently purified from media of cultured mouse fibroblasts. Kessler et al., 1986, Collagen Relat. Res. 6:249–266; Kessler and Adar, 1989, Eur. J. Biochem. 186:115–121.

Experiments conducted with these purified forms of chick and mouse C-proteinase have indicated that the enzyme is instrumental in the formation of functional collagen fibers. Fertala et al., 1994, J. Biol. Chem. 269:11584.

Generally, C-proteinase activity and the inhibition of the enzyme's activity have been determined using a wide array of assays. See e.g., Kessler and Goldberg, 1978, Anal. Biochem. 86:463; Njieha et al., 1982, Biochemistry 21:757–764. As articulated in numerous publications, the enzyme is difficult to isolate by conventional biochemical means and neither the enzyme nor the cDNA sequence encoding such enzyme was known to be available prior to the instant invention. Takahara et al., 1994, J. Biol. Chem. 269:26280–26285, 26284 (C-proteinase's "peptide and nucleotide sequences are as yet unavailable"). Thus, despite the availability of C-proteinase related assays, large scale review and testing of potential C-proteinase inhibitors has not been performed to date.

Known C-Proteinase Inhibitors. A number of potential C-proteinase inhibitors have been identified. For example, several metal chelators have demonstrated activity as a C-proteinase inhibitor. Likewise, chymostatin and pepstatin A have been found to act as relatively strong inhibitors of C-proteinase activity.

$\alpha_2$-Macroglobulin, ovostatin, and fetal bovine serum appear to also, at least partially, inhibit C-proteinase activity. Similarly, dithiothreitol, SDS, concanavalin A, $Zn^{2+}$, $Cu^{2+}$, and $Cd^{2+}$ possess inhibitory activity at low concentrations, and some reducing agents, several amino acids (including lysine and arginine), phosphate, and ammonium sulfate have been found to have C-proteinase inhibitory activity at concentrations of 1–10 mM. Leung et al., supra; Ryhänen et al., 1982, Arch. Biochem. Biophys. 215:230–236.

High concentrations of NaCl or Tris-HCl buffer have also been found to inhibit the C-proteinase activity. For example, it has been reported that 0.2, 0.3, and 0.5M NaCl reduces the activity of C-proteinase by 66, 38, and 25%, respectively, of that observed with the standard assay concentration of 0.15M. Tris-HCl buffer in a concentration of 0.2–0.5M likewise has been reported to inhibit the enzyme's activity. Hojima et al., supra.

In contrast, microbial inhibitors such as leupeptin, phosphoramidon, antipain, bestatin, elastinal, and amastatin, are considered to have weak or no effect.

Background Information Regarding Bone Morphogenic Protein-1 (BMP-1). A protein having the structural characteristics of C-proteinase was isolated in 1988 from bone tissue. Prior to the instant invention, it was believed that this protein, designated BMP-1 or "bone morphogenic protein," was a member of the TGF-β related protein family (Wozney et al., 1988, Science 242:1528–1534), as BMP-1 was isolated coincidentally with BMP-2A and BMP-3. Although evidence provides that BMP-2A and BMP-3 play a key role in the stimulation of bone development and growth, the activity of BMP-1 was never clearly established.

Sequence comparison reveals that BMP-1 contains a EGF-like domain and a region designated as "A-domain" having sequence similarity with a protease isolated from crayfish. Titany et al., 1987, Biochemistry 26:222. As the TGF-β1 binding protein also contains EGF-like domains, it has been suggested that BMP-1 could be a protease involved in the activation of TGF-β1. Miyazono et al., 1988, J. Biol. Chem. 263:6407; Woyznek et al., supra; Fukagawa et al., 1994, Dev. Bio. 162:175–183.

It has also been suggested that, due to homology to the Drosophila melanogaster tolloid gene product, BMP-1 is involved in the overall mechanism for the dorsal-ventral patterning of the neural tube.

While it has been suggested that C-proteinase ("for which [prior to this invention] peptide and nucleotide sequence are as yet unavailable") and BMP-1 belong to the same structural family, BMP-1 has never been associated with the formation of collagen. Takahara et al., 1994, J. Biol. Chem. 269:26280–26286. Thus, while a cDNA and polypeptide sequence of the putative bone morphogenic protein BMP-1 had been identified, no correct activity or use was known for this protein until the present invention. Similarly, the structural relationship between BMP-1 and C-proteinase was not known.

4. SUMMARY OF THE INVENTION

The present invention is directed to synthesized or recombinant compositions derived from the deduced amino acid and nucleic acid sequences for human C-proteinase. In one embodiment of the present invention, the composition comprises the full-length amino acid sequence for C-proteinase. In another embodiment of the present invention, the composition comprises a C-proteinase derivative having C-proteinase-like activity. In yet further embodiments of the present invention, the composition is radiolabeled or represents an analog of C-proteinase having C-proteinase-like activity. The present invention is also related to the recombinant production of C-proteinase and related compositions in a variety of recombinant expression systems.

The present invention also relates to the use C-proteinase, its fragments, analogs and derivatives for use in diseases and disorders related to the abnormal production of collagen. Such polypeptides may act directly with collagen, or alternatively with other enzymes involved in the processing of collagen, i.e., lysyl oxidase.

The present invention also relates to the use of proteins, peptides and organic molecules capable of modulating the formation of collagen by affecting the interaction between C-proteinase and collagen precursor molecules, including procollagen, or alternatively, other collagen processing enzymes and/or the cleavage site of C-proteinase. The invention is further directed to the use of such proteins, peptides and/or organic molecules, either alone or in combination with other molecules, in the treatment of disorders, including disorders related to abnormal collagen formation, such as rheumatoid arthritis and scleroderma, for example.

The present invention is also related to the use of C-proteinase, whether labeled or unlabeled, as a tracer which could then be used to separate, by HPLC, the different C-proteinase derivatives to yield a carrier-free tracer, in binding assays.

Finally, the present invention is related to the recombinant expression and production of C-proteinase by use of the sequences of the invention.

5. DEFINITIONS

"C-proteinase" shall be construed to mean an enzyme capable of processing collagen molecules, derivatives or fragments, or their precursors by cleaving through -Alas↓Asp-Asp- and/or -Gly↓Asp-Glu-. The term shall include human C-proteinase and derivatives, analogs, fragments and variants thereof having C-proteinase-like activity.

6. BRIEF DESCRIPTION OF THE DRAWINGS

FIG. 1 (FIG. 1) generally sets forth the sequenced peptides from procollagen C-proteinase, the encoded structures of pCP-1 and pCP-2, and isolated cDNA clones.

FIG. 1A identifies the peptides sequenced from which pCP and described below at Table 1.

Figure 1B:
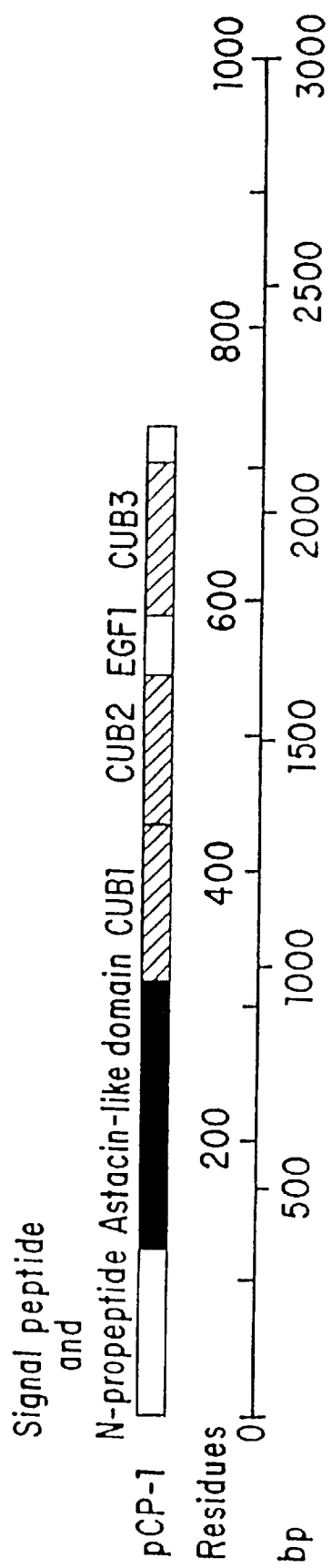

FIG. 1B identifies the domains encoded for pCP-1.

Figure 1C:
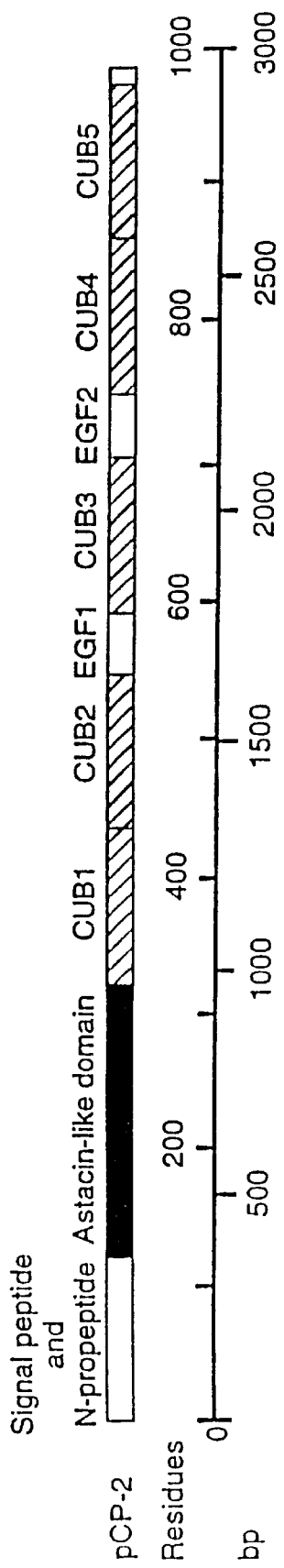

FIG. 1C identifies the domains encoded for pCP-2.

Figure 1D:
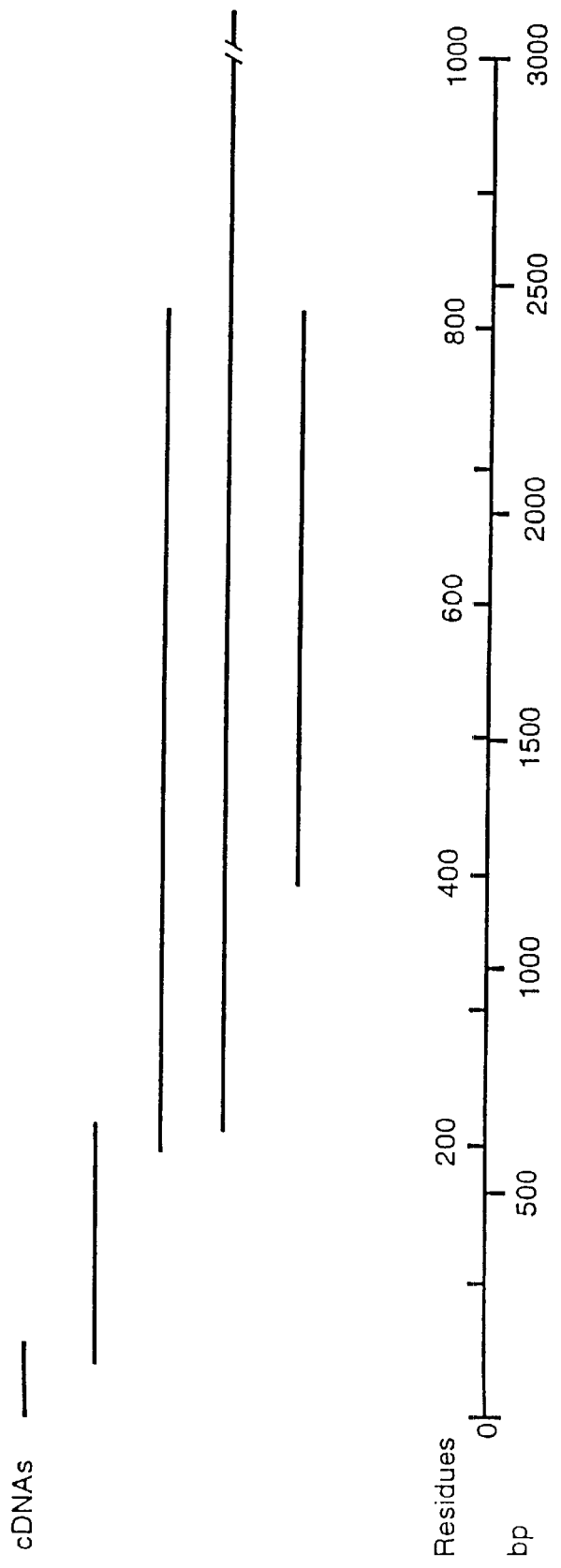

FIG. 1D identifies the regions of cDNAs obtained according to the scheme set forth below.

Figure 2:
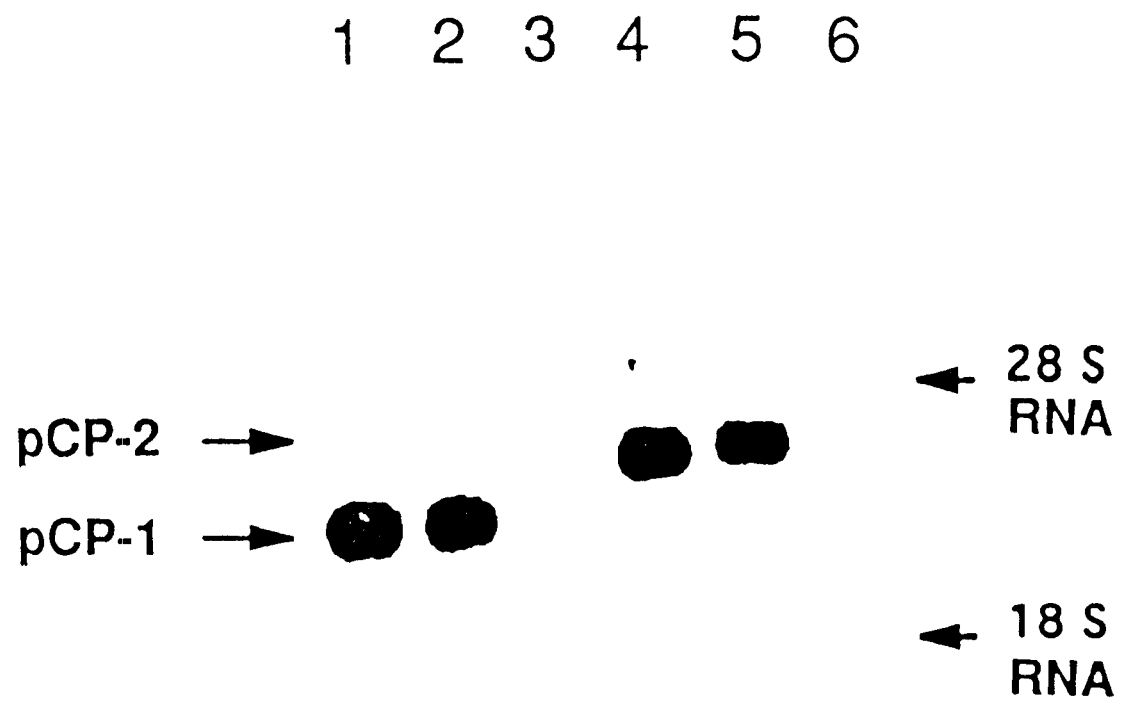

FIG. 2 (FIG. 2) sets forth a Northern blot assay of total RNA from HT-1080 cells wherein the filter was probed with a $^{32}$P-labeled clone of pCP-1 (nucleotides 837 to 2487, wherein said clone was labeled by random primer extension with $^{32}$p to a specific activity of $4\times10^8$ cpm per μg). The filter was exposed to X-ray film at −70° C. for six hours. Lanes 1 and 2 provide two clones transfected with pCP-1; lane 3 provides a clone transfected with the vector pcDNA-3 without a cDNA insert; lanes 4 and 5 set forth two clones transfected with pCP-2; and lane 6 sets forth RNA from untransfected HT-1080 host cells.

Figure 3:
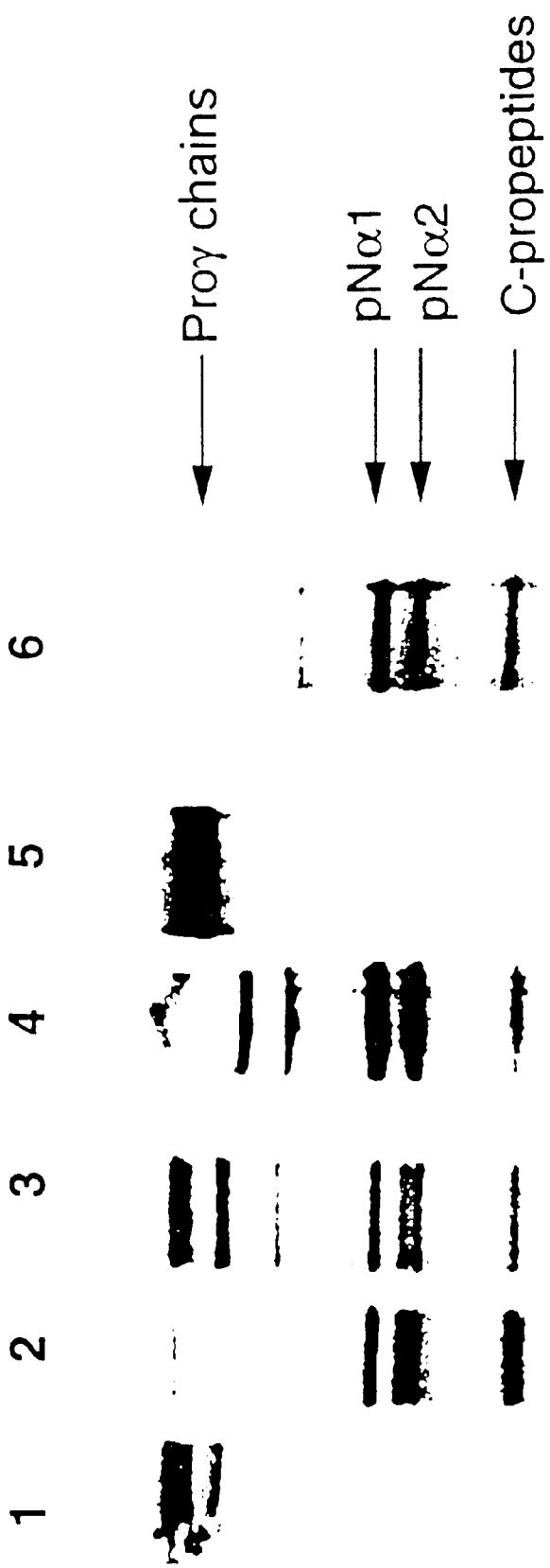

FIG. 3 (FIG. 3) sets forth the results of an assay conducted to determine C-proteinase activity in medium from transfected cells. Lane 1 provides $^{14}$C-labeled type I procollagen, incubated alone; lane 2 provides $^{14}$C-labeled type I procollagen, incubated with 10 units of purified chick procollagen C-proteinase; lane 3 provides $^{14}$C-labeled type I procollagen, incubated with proteins precipitated by PEG from 15 ml of medium from a clone transfected with pCP-1; lane 4 provides $^{14}$C-labeled type I procollagen, incubated with proteins precipitated by PEG from 15 ml of medium from a clone transfected with pCP-2 lane 5 provides $^{14}$C-labeled type I procollagen, incubated with proteins precipitated by PEG from 15 ml of medium from non-transfected HT-1080 host cells; lane 6 provides $^{14}$C-labeled type I procollagen, incubated with proteins partially fractionated and concentrated by membrane filtration from 10 ml of medium from a clone transfected with pCP-2.

Figure 4:
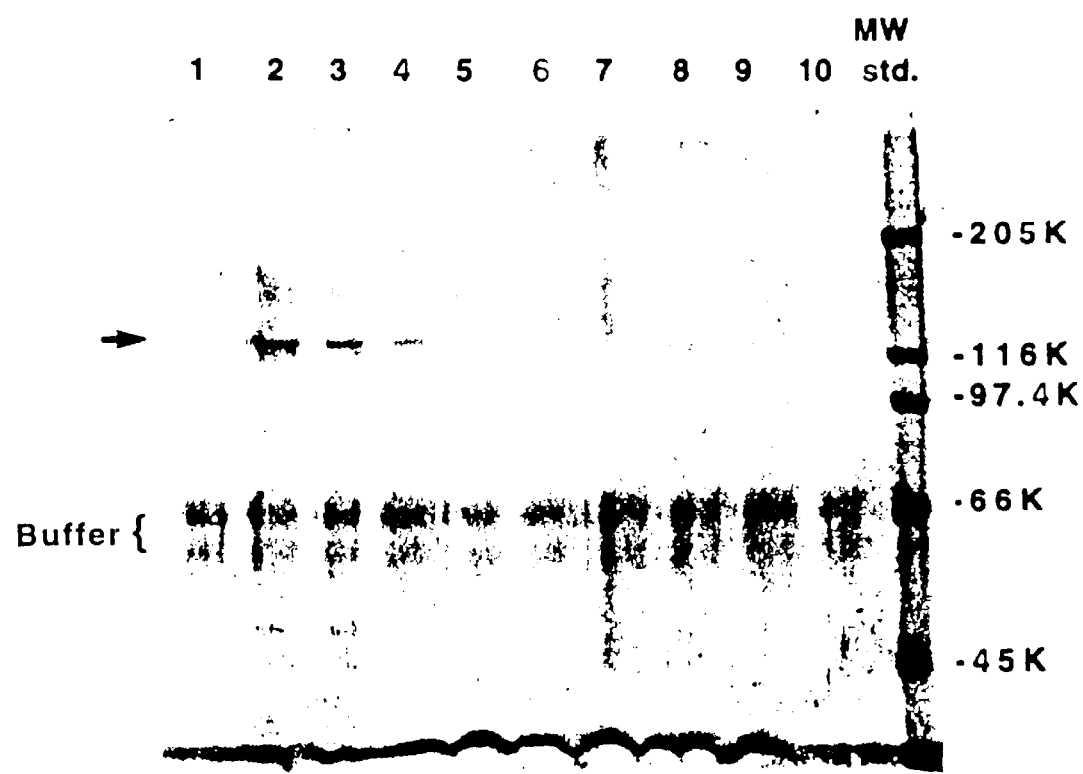

FIG. 4 (FIG. 4) sets forth a chromatograph of extract from *E. coli* on a metal affinity column.

Figure 5:
Figure 5:

FIG. 5 (FIG. 5) sets forth the results of an assay conducted to determine C-proteinase activity of the recombinant protein expressed in *E. coli*. Lanes 1 and 2 provide $^{14}$C-labeled procollagen (0.2 µg; 4000 cpm) incubated in reaction buffer for fifteen (15) hours at 35° C. with 0.2 µg refolded recombinant protein activated by prior digestion for two (2) hours at 37° C. with 10 µg/ml chymotrypsin. Lanes 3 and 4 provide 14C-labeled procollagen (0.2 µg; 4000 cpm) incubated in reaction buffer for 15 hours at 35° C. with 0.2 µg refolded recombinant protein activated by digestion with 100 µg/ml chymotrypsin. Lane 5 provides 14C-labeled procollagen, incubated without enzyme. Lane 6 provides $^{14}$C-labeled procollagen, incubated with procollagen C-proteinase from chick embryos (0.2 units; 0.006 µg).

FIGS. 6A–E collectively set forth the nucleic acid sequence (SEQ ID NO:1) and amino acid sequence (SEQ ID NO:2) of pCP-1.

FIGS. 7A–G collectively set forth the nucleic acid sequence (SEQ ID NO:3) and amino acid sequence (SEQ ID NO:4) of pCP-2.

7. DETAILED DESCRIPTION OF THE INVENTION 7.1. Isolation of Gene Encoding C-Proteinase The C-proteinase enzyme may be isolated to homogeneity by application of previously described procedures, including the procedures described in Hojima, et al., 1985, *J. Biol. Chem.* 260:15996. In a preferred embodiment, the protein is purified using the method of Hojima, et al. and a final purification step in which protein separation is accomplished by polyacrylamide gel electrophoresis in SDS.

The homogenous C-proteinase enzyme may then be sequenced according to known techniques using commercially available apparatus. In one preferred method, tryptic peptides from the gel band containing the enzyme were sequenced by: (1) electroeluting the protein band onto a filter; (2) digesting the band in situ with trypsin; (3) separating the tryptic peptides using a reverse phase C18 column (Supelco LC18DB) eluted with a gradient of 0.1% trifluoroacetic acid and 0.9% trifluoroacetic acid containing 70% acetonitrile; (4) assaying the individual peaks from the column for homogeneity by time-of-flight-matrix-assisted laser desorption mass spectrometry (Lasermat; Finnigan); and (5) sequencing the homogeneous fractions by Edman degradation.

Nucleic acid probes may be prepared using the determined amino acid sequence for C-proteinase. Such probes may be synthesized synthetically and labeled. Preparation techniques for such probes and others are known in the art and set forth in, for example, Sambrook, et al., 1989, *Molecular Cloning, A Laboratory Manual,* 2d Edition, Cold Springs Harbor Laboratory Press, New York, at Chapters 10–11. The nucleic acid sequences obtained using such probes may be sequenced using any one of the techniques generally described in Sambrook, et al., supra, at Chapter 13.

The gene encoding C-proteinase may also be isolated by performing a polymerase chain reaction (PCR) using one or more degenerate oligonucleotide primer pools that are designed based on the deduced nucleotide sequence of C-proteinase, as deduced from the amino acid sequence of C-proteinase. The techniques used to identify the nucleic acid sequence of C-proteinase using PCR are described in, for example, Sambrook, et al., supra, at Chapter 14.

The invention also relates to unknown C-proteinase genes isolated from other species and alleles of the C-proteinase gene described herein, in which C-proteinase activity exists. Members of the C-proteinase family are defined herein as those enzymes that can process procollagen molecules at the C-terminal end of such molecule. A bacteriophage cDNA library may be screened, under conditions of reduced stringency, using a radioactively labeled fragment of the human C-proteinase clone described herein. Alternatively the human C-proteinase sequence can be used to design degenerate or fully degenerate oligonucleotide probes which can be used as PCR probes or to screen bacteriophage cDNA libraries. The PCR product may be subcloned and sequenced to insure that the amplified sequences represent the C-proteinase sequences. The PCR fragment may be used to isolate a full length C-proteinase clone by radioactively labeling the amplified fragment and screening a bacteriophage cDNA library. Alternatively, the labeled fragment may be used to screen a genomic library. For a review of cloning strategies which may be used, see e.g., Sambrook, et al., 1989, *Molecular Cloning, A Laboratory Manual,* 2d Edition, Cold Springs Harbor Press, N.Y.; and Ausubel et al., 1989, Current Protocols in Molecular Biology, (Green Publishing Associates and Wiley Interscience, N.Y.)

Isolation of human C-proteinase cDNA may also be achieved by construction of a cDNA library in a mammalian expression vector such as pcDNA1, that contains SV40 origin of replication sequences which permit high copy number expression of plasmids when transferred into COS cells. The expression of C-proteinase on the surface of transfected COS cells may be detected in a number of ways known in the art. Cells expressing the human C-proteinase may be enriched by subjecting transfected cells to a FACS (fluorescent activated cell sorter) sort.

In accordance with the invention, C-proteinase nucleotide sequences which encode C-proteinase, peptide fragments of C-proteinase, C-proteinase fusion proteins or functional equivalents thereof may be used to generate recombinant DNA molecules that direct the expression of the protein or a functional equivalent thereof, in appropriate host cells. Alternatively, nucleotide sequences which hybridize to portions of the C-proteinase sequence may also be used in nucleic acid hybridization assays, Southern and Northern blot analyses, etc.

Due to the inherent degeneracy of the genetic code, other DNA sequences which encode substantially the same or a functionally equivalent amino acid sequence, may be used in the practice of the invention for the cloning and expression of the C-proteinase protein. Such DNA sequences include those which are capable of hybridizing to the human C-proteinase sequence under stringent conditions, and more preferably highly stringent conditions. See, e.g., Wallace et al., 1981, *Nucleic Acid Research* 9:879.

Altered DNA sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues within the C-proteinase sequence, which result in a silent change thus producing a functionally equivalent protein. Such amino acid substitutions may be made on the basis of similarity in polarity, charge, solubility, hydrophobicity, hydrophilicity, and/or the amphipatic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine, glycine, analine, asparagine, glutamine, serine, threonine; phenylalanine, tyrosine. As used herein, a functionally equivalent C-proteinase refers to an enzyme which can process procollagen or fragments or derivatives thereof, but not necessarily with the same binding affinity of its counterpart native C-proteinase.

The DNA sequences of the invention may be engineered in order to alter the enzyme sequence for a variety of ends including but not limited to alterations which modify processing and expression of the gene product. For example, mutations may be introduced using techniques which are well known in the art, e.g., site-directed mutagenesis to, for example, insert new restriction sites. For example, in certain expression systems such as yeast, host cells may over-glycosylate the gene product. When using such expression systems it may be preferable to alter the C-proteinase coding sequence to eliminate any N-linked glycosylation site.

In another embodiment of the invention, the C-proteinase or a modified C-proteinase sequence may be ligated to a heterologous sequence to encode a fusion protein. For example, for screening of peptide libraries it may be useful to encode a chimeric C-proteinase protein expressing a heterologous epitope that is recognized by a commercially available antibody. A fusion protein may also be engineered to contain a cleavage site located between the C-proteinase sequence and the heterologous protein sequence, so that the C-proteinase can be cleaved away from the heterologous moiety.

In an alternate embodiment of the invention, the coding sequence of C-proteinase could be synthesized in whole or in part, using chemical methods well known in the art. See, for example, Caruthers et al., 1980, *Nucleic Acids Res. Symp. Ser.* 7:215–233; Crea and Horn, 1980, *Nucleic Acids Res.* 9:2331; Matteucci and Caruthers, 1980, *Tetrahedron Letters* 21:719; and Chow and Kempe, 1981, *Nucleic Acids Res.* 9:2807–2817. Alternatively, the protein itself could be produced using chemical methods to synthesize the C-proteinase amino acid sequence in whole or in part. For example, peptides can be synthesized by solid phase techniques, cleaved from the resin, and purified by preparative high performance liquid chromatography. (See, e.g., see Creighton, 1983, *Proteins Structures And Molecular Principles,* W. H. Freeman and Co., N.Y. pp. 50–60). The composition of the synthetic peptides may be confirmed by amino acid analysis or sequencing (e.g., the Edman degradation procedure; see, Creighton, 1983, *Proteins, Structures and Molecular Principles,* W. H. Freeman and Co., N.Y., pp. 34–49).

7.2. Uses of the C-Proteinase Coding Sequence

The C-proteinase coding sequence may be used for diagnostic purposes for detection of C-proteinase expression. Included in the scope of the invention are oligoribonucleotide sequences, that include antisense RNA and DNA molecules and ribozymes that function to inhibit translation of C-proteinase. Antisense techniques are known in the art and may be applied herein.

Ribozymes are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. Within the scope of the invention are engineered hammerhead motif ribozyme molecules that specifically and efficiently catalyze endonucleolytic cleavage of C-proteinase RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between fifteen (15) and twenty (20) ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Both antisense RNA and DNA molecules and ribozymes of the invention may be prepared by any method known in the art for the synthesis of RNA molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

In addition, mutated forms of C-proteinase, having a dominant negative effect, may be expressed in targeted cell populations to inhibit the activity of endogenously expressed wild-type C-proteinase.

Additionally, the DNA encoding C-proteinase may also have a number of uses for the diagnosis of diseases resulting from aberrant expression of the enzyme. For example, the C-proteinase DNA sequence may be used in hybridization assays of biopsies or autopsies to diagnose abnormalities of expression (e.g., Southern or Northern blot analysis, in situ hybridization assays).

The C-proteinase cDNA may be used also as a probe to detect the expression of the C-proteinase mRNA.

In addition, the expression of C-proteinase during embryonic development may also be determined using nucleic acid encoding C-proteinase. As described in the literature, no deficiencies of C-proteinase have been found in patients with genetic diseases of connective tissues. Thus, it has been generally assumed that a genetic deficiency related to C-proteinase produces death in utero. In situ hybridizations can predict in utero problems related to connective tissue diseases.

Various modifications to the DNA molecules may be introduced as a means of increasing intracellular stability and half-life. Possible modifications include but are not limited to the addition of flanking sequences of ribo- or deoxynucleotides to the 5' and/or 3' ends of the molecule or the use of phosphorothioate or 2' O-methyl rather than phosphodiesterase linkages within the oligodeoxyribonucleotide backbone.

7.3. Expression of C-Proteinase

In order to express a biologically active C-proteinase, the nucleotide sequence coding for the protein, or a functional equivalent as described in Section 4.1 supra, was inserted into an appropriate expression vector, i.e., a vector which contains the necessary elements for the transcription and translation of the inserted coding sequence.

More specifically, methods which are well known to those skilled in the art can be used to construct expression vectors containing the C-proteinase sequence and appropriate transcriptional/translational control signals. These methods include in vitro recombinant DNA techniques, synthetic techniques and in vivo recombination/genetic recombination. See e.g., the techniques described in Sambrook et al., 1989, *Molecular Cloning A Laboratory Manual*, Cold Spring Harbor Laboratory, N.Y. and Ausubel et al., 1989, *Current Protocols in Molecular Biology*, Greene Publishing Associates and Wiley Interscience, N.Y.

A variety of host-expression vector systems may be utilized to express the C-proteinase coding sequence. These include but are not limited to microorganisms such as bacteria transformed with recombinant bacteriophage DNA, plasmid DNA or cosmid DNA expression vectors containing the C-proteinase coding sequence; yeast transformed with recombinant yeast expression vectors containing the C-proteinase coding sequence; insect cell systems infected with recombinant virus expression vectors (e.g., baculovirus) containing the C-proteinase coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the C-proteinase coding sequence; or animal cell systems infected with recombinant virus expression vectors (e.g., adenovirus, vaccinia virus, human tumor cells (including HT-1080)) including cell lines engineered to contain multiple copies of the C-proteinase DNA either stably amplified (CHO/dhfr) or unstably amplified in double-minute chromosomes (e.g., murine cell lines). In the preferred embodiments of the invention, HT-1080 and *E. coli* were used as expression vehicles.

The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the C-proteinase DNA SV40-, BPV- and EBV-based vectors may be used with an appropriate selectable marker.

In bacterial systems, a number of expression vectors may be advantageously selected depending upon the use intended for the C-proteinase expressed. For example, when large quantities of C-proteinase are to be produced to screen peptide libraries, vectors which direct the expression of high levels of fusion protein products that are readily purified may be desirable. Such vectors include but are not limited to the *E. coli* expression vector pUR278 (Ruther et al., 1983, *EMBO J.* 2:1791), in which the C-proteinase coding sequence may be ligated into the vector in frame with the lac Z coding region so that a hybrid AS-lac Z protein is produced; pIN vectors (Inouye and Inouye, 1985, *Nucleic Acids Res.* 13:3101–3109; Van Heeke and Schuster, 1989, *J. Biol. Chem.* 264:5503–5509), and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned polypeptide of interest can be released from the GST moiety.

In yeast, a number of vectors containing constitutive or inducible promoters may be used. For a review, see, *Current Protocols in Molecular Biology*, Vol. 2, 1988, Ed. Ausubel et al., Greene Publish. Assoc. & Wiley Interscience, Ch. 13; Grant et al., 1987, *Expression and Secretion Vectors for Yeast*, in Methods in Enzymology, Eds. Wu & Grossman, 1987, Acad. Press, N.Y., Vol. 153, pp. 516–544; Glover, 1986, *DNA Cloning*, Vol. II, IRL Press, Wash., D.C., Ch. 3; Bitter, 1987, *Heterologous Gene Expression in Yeast*, Methods in Enzymology, Eds. Berger & Kimmel, Acad. Press, N.Y., Vol. 152, pp. 673–684; and *The Molecular Biology of the Yeast Saccharomyces,* 1982, Eds. Strathern et al., Cold Spring Harbor Press, Vols. I and II.

In cases where plant expression vectors are used, the expression of the C-proteinase coding sequence may be driven by any of a number of promoters. For example, viral promoters such as the 35S RNA and 19S RNA promoters of CaMV (Brisson et al., 1984, *Nature* 310:511–514), or the coat protein promoter of TMV (Takamatsu et al., 1987, *EMBO J.* 6:307–311) may be used; alternatively, plant promoters such as the small subunit of RUBISCO (Coruzzi et al., 1984, *EMBO J.* 3:1671–1680; Broglie et al., 1984, *Science* 224:838–843); or heat shock promoters, e.g., soybean hsp17.5-E or hsp17.3-B (Gurley et al., 1986, *Mol. Cell. Biol.* 6:559–565) may be used. These constructs can be introduced into plant cells using Ti plasmids, Ri plasmids, plant virus vectors, direct DNA transformation, microinjection, electroporation, etc. For reviews of such techniques, see, for example, Weissbach and Weissbach, 1988, *Methods for Plant Molecular Biology*, Academic Press, NY, Section VIII, pp. 421–463; and Grierson and Corey, 1988, *Plant Molecular Biology,* 2d Ed., Blackie, London, Ch. 7–9.

An alternative expression system which could be used to express C-proteinase is an insect system. In one such system, Baculovirus is used as a vector to express foreign genes. The virus then grows in the insect cells. The C-proteinase coding sequence may be cloned into non-essential regions (for example the polyhedron gene) of the virus and placed under control of a Baculovirus promoter. These recombinant viruses are then used to infect insect cells in which the inserted gene is expressed. (E.g., see, Smith et al., 1983, *J. Viol.* 46:584; Smith, U.S. Pat. No. 4,215,051).

In mammalian host cells, a number of viral based expression systems may be utilized. In cases where an adenovirus is used as an expression vector, the C-proteinase coding sequence may be ligated to an adenovirus transcription/ translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing C-proteinase in infected hosts. See, e.g., Logan and Shenk, 1984, *Proc. Natl. Acad. Sci. USA* 81:3655–3659. Alternatively, the vaccinia 7.5K promoter may be used. See, e.g., Mackett et al., 1982, *Proc. Natl. Acad. Sci. USA* 79:7415–7419; Mackett et al., 1984, *J. Virol.* 49:857–864; Panicali et al., 1982, *Proc. Natl. Acad. Sci. USA* 79:4927–4931.

In a preferred embodiment, the C-proteinase sequence is expressed in human tumor cells, and more preferably HT-1080, which have been stably transfected with calcium phosphate precipitation and a neomycin resistance gene.

Specific initiation signals may also be required for efficient translation of inserted C-proteinase coding sequences. These signals include the ATG initiation codon and adjacent sequences. In cases where the entire C-proteinase gene, including its own initiation codon and adjacent sequences, is inserted into the appropriate expression vector, no additional translational control signals may be needed. However, in cases where only a portion of the C-proteinase coding sequence is inserted, exogenous translational control signals, including the ATG initiation codon, must be provided. Furthermore, the initiation codon must be in phase with the reading frame of the C-proteinase coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. See, e.g., Bitter et al., 1987, *Methods in Enzymol.* 153:516–544.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, WI38, HT-1080 etc.

For long-term, high-yield production of recombinant proteins, stable expression is preferred. For example, cell lines which stably express C-proteinase may be engineered. Rather than using expression vectors which contain viral origins of replication, host cells can be transformed with C-proteinase DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including but not limited to the herpes simplex virus thymidine kinase (Wigler et al., 1977, *Cell* 11:223), hypoxanthine-guanine phosphoribosyltransferase (Szybalska and Szybalski, 1962, *Proc. Natl. Acad. Sci. USA* 48:2026), and adenine phosphoribosyltransferase (Lowy et al., 1980, *Cell* 22:817) genes can be employed in tk$^-$, hgprt$^-$ or aprt$^-$cells, respectively. Also, antimetabolite resistance can be used as the basis of selection for dhfr, which confers resistance to methotrexate (Wigler et al., 1980, *Proc. Natl. Acad. Sci. USA* 77:3567; O'Hare et al., 1981, *Proc. Natl. Acad. Sci. USA* 78:1527); gpt, which confers resistance to mycophenolic acid (Mulligan and Berg, 1981, *Proc. Natl. Acad. Sci. USA* 78:2072); neo, which confers resistance to the aminoglycoside G-418 (Colberre-Garapin et al., 1981, *J. Mol. Biol.* 150:1); and hygro, which confers resistance to hygromycin (Santerre et al., 1984, *Gene* 30:147) genes. Recently, additional selectable genes have been described, namely trpB, which allows cells to utilize indole in place of tryptophan; hisD, which allows cells to utilize histinol in place of histidine (Hartman and Mulligan, 1988, *Proc. Natl. Acad. Sci. USA* 85:8047), and ODC (ornithine decarboxylase) which confers resistance to the ornithine decarboxylase inhibitor, 2-(difluoromethyl)-DL-ornithine, DFMO (McConlogue, 1987, In: *Current Communications in Molecular Biology*, Cold Spring Harbor Laboratory ed.).

7.4. Identification of Transfectants or Transformants that Express C-Proteinase

The host cells which contain the coding sequence and which express the biologically active gene product may be identified by at least four general approaches: (a) DNA—DNA or DNA-RNA hybridization; (b) the presence or absence of "marker" gene functions; (c) assessing the level of transcription as measured by the expression of C-proteinase mRNA transcripts in the host cell; and (d) detection of the gene product as measured by an assay or by its biological activity.

In the first approach, the presence of the C-proteinase coding sequence inserted in the expression vector can be detected by DNA—DNA or DNA-RNA hybridization using probes comprising nucleotide sequences that are homologous to the C-proteinase coding sequence, respectively, or portions or derivatives thereof.

In the second approach, the recombinant expression vector/host system can be identified and selected based upon the presence or absence of certain "marker" gene functions (e.g., resistance to antibiotics, resistance to methotrexate, transformation phenotype, occlusion body formation in baculovirus, etc.). For example, in a preferred embodiment, the C-proteinase coding sequence is inserted within a neomycin-resistance marker gene sequence of the vector, and recombinants containing the C-proteinase coding sequence can be identified by the absence of the marker gene function. Alternatively, a marker gene can be placed in tandem with the C-proteinase sequence under the control of the same or different promoter used to control the expression of the C-proteinase coding sequence. Expression of the marker in response to induction or selection indicates expression of the C-proteinase coding sequence.

In the third approach, transcriptional activity for the C-proteinase coding region can be assessed by hybridization assays. For example, RNA can be isolated and analyzed by Northern blot using a probe homologous to the C-proteinase coding sequence or particular portions thereof. Alternatively, total nucleic acids of the host cell may be extracted and assayed for hybridization to such probes.

The fourth approach involves the detection of the biologically active C-proteinase gene product. A number of assays can be used to detect C-proteinase activity, including, but not limited to, those assays described in Kessler and Goldberg, 1978, *Anal. Biochem.* 86:463; and Njieha et al., 1982, *Biochemistry* 21:757–764.

7.5. Screening of Peptide Library with C-Proteinase or Engineered Cell Lines

Random peptide libraries consisting of all possible combinations of amino acids attached to a solid phase support may be used to identify peptides that are able to modulate and/or inhibit C-proteinase activity by binding to C-proteinase. The screening of peptide libraries may have therapeutic value in the discovery of pharmaceutical agents that act to inhibit the biological activity of the protein.

Identification of molecules that are able to bind to C-proteinase may be accomplished by screening a peptide library with recombinant soluble C-proteinase. Methods for expression and purification of the enzyme are described above and may be used to express recombinant full length C-proteinase or fragments, analogs, or derivatives thereof depending on the functional domains of interest.

To identify and isolate the peptide/solid phase support that interacts and forms a complex with C-proteinase it is necessary to label or "tag" the C-proteinase molecule. The C-proteinase protein may be labeled according to well-known techniques, including iodination labelling with $^{125}$I. Additionally, the C-proteinase protein also may be conjugated to enzymes such as alkaline phosphatase or horseradish peroxidase or to other reagents such as fluorescent labels which may include fluorescein isothyiocynate (FITC), phycoerythrin (PE) or rhodamine. Conjugation of any given label, to C-proteinase, may be performed using techniques that are routine in the art. Alternatively, C-proteinase expression vectors may be engineered to express a chimeric protein containing an epitope for which a commercially available antibody exist. The epitope specific antibody may be tagged using methods well known in the art including labeling with enzymes, fluorescent dyes or colored or magnetic beads.

The "tagged" C-proteinase is incubated with the random peptide library for 30 minutes to one hour at 22° C. to allow complex formation between C-proteinase and peptide species within the library. The library is then washed to remove any unbound protein. If C-proteinase has been conjugated to alkaline phosphatase or horseradish peroxidase the whole library is poured into a petri dish containing a substrates for either alkaline phosphatase or peroxidase, for example, 5-bromo-4-chloro-3-indoyl phosphate (BCIP) or 3,3',4,4"-diamnobenzidine (DAB), respectively. After incubating for several minutes, the peptide/solid phase-C-proteinase complex changes color, and can be easily identified and isolated physically under a dissecting microscope with a micromanipulator. If a fluorescent tagged C-proteinase molecule has been used, complexes may be isolated by fluorescent activated sorting. If a chimeric C-proteinase expressing a heterologous epitope has been used, detection of the peptide/C-proteinase complex may be accomplished by using a labeled epitope specific antibody. Once isolated, the identity of the peptide attached to the solid phase support may be determined by peptide sequencing.

7.6. Screening of Organic Compounds with C-Proteinase Protein or Engineered Cell Lines Cell lines that express C-proteinase may be used to screen for molecules that modulate C-proteinase activity or collagen formation. Such molecules may include small organic or inorganic compounds, or other molecules that modulate C-proteinase activity or that promote or prevent the formation of collagen. Synthetic compounds, natural products, and other sources of potentially biologically active materials can be screened in a number of ways.

The ability of a test molecule to interfere with C-proteinase-procollagen binding and/or C-proteinase-processing enzyme binding may be measured using standard biochemical techniques. Other responses, such as activation or suppression of catalytic activity may also be monitored. These assays may be performed using conventional techniques developed for these purposes in the course of screening.

Various embodiments are described below for screening, identification and evaluation of compounds that interact with C-proteinase or its targets, which compounds may affect various cellular processes including the formation and production of collagen.

The following preparations and examples are given to enable those skilled in the art to more clearly understand and to practice the present invention. The present invention is not to be limited in scope by the exemplified embodiments which are intended as illustrations of single aspects of the invention, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

8. EXAMPLES 8.1. Identification of Partial Amino Acid Sequences of the C-Proteinase Type I procollagen C-proteinase was purified to homogeneity from organ cultures of chick embryo according to the methods set forth in Hojima et al., 1985, *J. Biol. Chem.* 260:15996–16003. In the final step, the protein was separated by polyacrylamide gel electrophoresis in SDS. The protein band was electroeluted onto a filter and digested in situ with trypsin. The tryptic peptides were separated on a reverse phase C18 column (Supelco LC18DB), and eluted with a gradient of 0.1% trifluoroacetic acid and 0.9% trifluoroacetic acid containing 70% acetonitrile. Individual peaks from the column were assayed for homogeneity by time-of-flight-matrix-assisted laser desorption mass spectrometry (Lasermat; Finnigan). Homogenous fractions were sequenced by Edman degradation with an automated instrument.

Nine sequences of different peptides were obtained, as set forth below in TABLE 1 and in FIG. 1A.

TABLE 1

| | | Amino Acid Position | |
|---|---|---|---|
| Peptide | Observed Sequence | BMP-1/ pCP-1 (SEQ ID NO:2) | tolloid-like BMP-1/pCP-2 (SEQ ID NO:4) |
| 1 | MEPQEVESLGETYDFDSIMH YAR | 252–274 | 252–274 |
| 2 | NTFSR | 275–279 | 275–279 |
| 3 | GIFLDT | 280–285 | 280–285 |
| 4 | EVN  KP YFEAGVRSPIGQR | 290–302 | 290–302 |
| 5 | T LPEPIVSSDSR | 401–411 | 401–411 |
| 6 | AYDYLEVR | 489–496 | 489–496 |
| 7 | LWLK | 525–528 | 525–528 |
| 8 | R  C  R EVDECSRPNNGGXEOK | 547–562 | 547–562 |

TABLE 1-continued

| Peptide | Observed Sequence | BMP-1/ pCP-1 (SEQ ID NO:2) | tolloid-like BMP-1/pCP-2 (SEQ ID NO:4) |
|---|---|---|---|
| | | Amino Acid Position | |
| 9 | NSGFVLHDMKHDCKEAGSEHR | CD K | 731–751 |

*Observed sequences are from tryptic peptides from chick pCP. Sequences above the continuous sequences are different are different amino acids encoded by human cDNAs.

With minor conservative substitutions attributable to the species difference, eight of the peptides contained sequences found in the protein initially identified as human BMP-1, as set forth in Wozney et al., *Science* 242:1528–1534. The ninth peptide had a sequence of 20 amino acids found in the C-terminal domain of one of the longer forms of BMP-1, as identified in mouse (Fukagawa et al., 1994, *Develop. Biol.* 163:175–183) and human (Takahara et al., 1994, *J. Biol. Chem.* 269:32572–32578) tissues.

8.2. Preparation and Structure of cDNAS for the C-Proteinase

To isolate cDNAs for procollagen C-proteinase, total RNA was extracted from normal human skin fibroblasts (RNAeasy; Qiagen) and reverse transcribed with random primers (First Strand cDNA Synthesis Kit; Pharmacia). The cDNA was amplified by PCR with a pair of primers designed on the basis of the amino acid sequence of two of the peptide fragments (peptides 1 and 6 in TABLE 1) from the chick C-proteinases, as described above. Specifically, the primers used were designated B-3 (ATGACTTCGACAGCATCATGC; SEQ ID NO:5) and B-4 (CTCCAGATAGTCGTAGGCACA; SEQ ID NO:6). The PCR product was $^{32}$P-labeled with random primers (Prime-It; Stratagene) and used as a probe to screen a cDNA library prepared from human skin fibroblasts (CRL 1262 (patient with osteogenesis imperfecta); ATCC) inserted into a lambda phage (ZAP II; Stratagene).

Five positive clones ranging in size from 0.16 to 2.9 kb were obtained (FIG. 1D). The most 3'-cDNA sequence extended to 3,560 base pairs. Analysis of overlapping sequences of the clones indicated that the cDNAs coded for two proteins of different length, one of 730 amino acids (pCP-1, see FIG. 6) and a second of 986 amino acids (pCP-2, see FIG. 7). The domains encoded by the two proteins, pCP-1 and pCP-2, are set forth at FIG. 1B and FIG. 1C, respectively. As set forth in FIGS. 1A and 1B, the first 702 codons for the two proteins were identical. Beginning with the codon for amino acid 703, however, pCP-2 had a new sequence that coded for a second EGF-like domain and a fourth and fifth CUB domain. The sequences of pCP-1 were identical to the previously published sequences of BMP-1 set forth in Wozney et al., supra, with the exception of the codon at amino acid position 24. Contrary to the BMP-1 sequence reported in Wozne, et al., supra, setting forth a -GAC- codon (encoding aspartate at amino acid position 24), the sequence obtained according to the above method included a -AAC- codon (encoding asparagine at amino acid position 24).

8.3. Expression of the cDNAs in a Mammalian Cell System

To express the cDNAs for procollagen C-proteinase, overlapping clones of the cDNAs were cleaved and ligated to generate full-length cDNAs. The cDNAs were inserted into the expression vector pcDNA3 (InVitrogen) and used to prepare stable transfectants of a HT-1080 human tumor cell line by calcium phosphate precipitation with a commercial kit (Promega).

Cells were initially cultured for twenty-four (24) hours in a high glucose DMEM medium containing 10% fetal bovine serum (Cellgrow; MediaTech) on 80 cm$^2$ culture dishes with 10$^6$ cells per dish. The cells were transfected by incubation for eighteen hours with a calcium phosphate precipitate containing 10 μg of the linearized plasmid. The cultures were incubated in fresh medium for an additional twenty-four (24) hours, passed after 1"10 dilution in 80 cm$^2$ dishes, and then grown under selection with 400 μg/ml of G418 (GIBCO/BRL) for twelve (12) days. Neomycin-resistant clones were transferred to 12-well microtiter plates, grown to confluency, and cultured in two 24-well plates for an additional twenty-four (24) hours. Total RNA was extracted from the cell layer in one well (RNAeasy; Qiagen) and used for Northern blot assay after separation by electrophoresis on a 1% agarose gel and transfer to nitrocellulose filters. The filters were probed using a $^{32}$P-labeled cDNA for the shortest cDNA for procollagen C-proteinase (pCP-1). Two clones, each transfected with pCP-1 or pCP-2, had high levels of corresponding mRNAs, as set forth in FIG. 2.

Medium from neomycin-resistant clones expressing either pCP-1 or pCP-2 contained enzymatic activity that specifically cleaved type I procollagen into the products predicted by the introduction of C-proteinase. Specifically, medium proteins from positive clones were fractionated either by PEG precipitation or by membrane filtration.

For PEG precipitation, 2×10$^7$ cells in 175 cm$^2$ flasks were incubated for 24 hours in serum-free DMEM and the medium (15 ml) was precipitated, as described above. The precipitated proteins were partially solubilized in 20 μl; of reaction buffer. For fractionation by membrane filtration, 30 ml of the medium were passed through a filter with a high molecular weight cut-off (XM300; Amicon). A second filter (50kDa Ultrafree 15; Millipore) was used to concentrate the flowthrough about 500-fold and to transfer the sample to reaction buffer. 20 μl of each sample was incubated at 35° C. for three (3) hours with 5 μl of reaction buffer containing 1 μg of $^{14}$C-labeled type I procollagen purified from chick embryo fibroblasts. The reaction products were separated on a 7.5-SDS-polyacrylamide gel without reduction and an image generated on a phosphor storage imager.

As set forth in FIG. 3, there was no detectable C-proteinase activity in medium from untransfected cells. Separation of the samples by polyacrylamide gel electrophoresis under reducing conditions demonstrated that the C1 subunit from the proα1 (I) chain and the C2 subunit from the proα1 (I) chain resembled the expected size and were obtained in the expected ratio of 2:1. Complete cleavage of type I procollagen to pNα1 (I) chains, pNα2 (I) chains and the C-propeptide were obtained with medium from a clone transfected with pCP-2 and partially fractionated and concentrated by membrane filtration (as set forth in lane 6 of FIG. 3).

8.4. Expression in an *E. coli* System

To express the protein in the *E. coli* system, a CDNA containing the complete coding sequences for PCP-2 was inserted into the expression vector that introduced as "tag" coding for 6 histidine residues at the 5'-end of the coding sequences (pQE-32 Vector; Qiagen). The vector was then used to transfect *E. coli* cells that were grown with and without induction with 1 Mm IPTG for one to four hours at 30° C. A protein band with an apparent molecular weight of about 100 kDa appeared in the cells induced with the IPTG.

The cell pellet was lysed in buffer containing lysozyme, sonicated, reincubated in lysis buffer containing Triton X-100 and then extracted with 6 M guanidine hydrochloride and 200 Mm NaCl in 10 Mm Tris-Hcl buffer (Ph 7.6). The solubilized protein was chromatographed on a metal affinity column (Talon; Clontech) and eluted with 100 Mm imidazole. The gel fractions were assayed by SDS PAGE and silver staining. As indicated in FIG. 4, the recombinant protein was recovered in apparently homogenous form.

To refold the protein, a method used to refold recombinant interstitial collagenase from *E. coli* inclusion bodies was used. Specifically, the protein from the metal affinity column was diluted to an intermediate strength of denaturant (2 M guanidine hydrochloride) so as to prevent precipitation but to allow formation of critical intermediates in the refolding process (see, e.g., Brems, 1988, *Biochemistry* 27:4541–4546; Ptitsyn, 1994, *Protein Eng.* 7:593–596). The protein was then dialyzed against a neutral isotonic buffer.

No C-proteinase activity was observed when the recombinant protein was incubated in a standard reaction system without prior activation of the protein by digestion with chymotrypsin. Specific C-proteinase activity was observed (Lanes 1 to 4 in FIG. 5) after limited digestion with chymotrypsin. The specific activity of the re-folded recombinant protein was about 1/30-th of the specific activity of C-proteinase isolated from chick embryo tendons (Lane 6 in FIG. 5). The yield of recombinant protein was about 2 mg/l.

8.5. Synthetic Substrates for C-Proteinase

Synthetic substrates for C-proteinase were obtained by testing a series of synthetic peptides with sequences found in and around the C-proteinase cleavage sites of -Ala-Asp- and -Gly-Asp- in the four proα chains of types 1, 11 and 111 procollagen (see, 11). Although it has been reported that at concentrations of 1 to 5 Mm the peptides competitively reduced cleavage of a $^{14}$C-labeled procollagen substrate, peptide cleavage was not originally detected using this reported concentration. When the enzyme concentration was increased 40- to 100-fold, the reaction time was concurrently increased from two (2) hours to eight (8) to twenty-four (24) hours, and the reaction products were analyzed by HPLC, followed by laser desorption mass spectrometry, four of the eight propeptides were specifically and completely cleaved by the enzyme.

All references cited within the body of the instant specification are hereby incorporated by reference in their entirety.

What is claimed:

1. A method for treating a disorder or disease related to fibrosis in a subject, the method comprising administering a compound that modulates C-proteinase activity such that collagen formation is affected.

2. The method of claim 1, wherein the compound increases C-proteinase activity.

3. The method of claim 1, wherein C-proteinase comprises the amino acid sequence of SEQ ID NO:2.

4. The method of claim 1, wherein C-proteinase comprises the amino acid sequence of SEQ ID NO:4.

5. The method of claim 1, wherein the disorder or disease is selected from the group consisting of hypertrophic scars, scar revision/plastic surgeries, joint adhesions, pelvic adhesions, rheumatoid arthritis, and scleroderma.

6. The method of claim 1, wherein the compound inhibits C-proteinase activity.

7. The method of claim 1, wherein the compound decreases C-proteinase activity.

8. The method of claim 1, wherein the compound comprises C-proteinase.

9. The method of claim 7, wherein the compound comprises a synthetic peptide substrate for C-proteinase.

10. The method of claim 9, wherein the peptide substrate contains a C-proteinase cleavage site selected from -Ala-Asp- or -Gly-Asp-.

* * * * *